(12) United States Patent
Liu et al.

(10) Patent No.: US 6,596,747 B2
(45) Date of Patent: Jul. 22, 2003

(54) COMPOUNDS DERIVED FROM AN AMINE NUCLEUS AND PHARMACEUTICAL COMPOSITIONS COMPRISING SAME

(75) Inventors: Chunjian Liu, Pennington, NJ (US); T. G. Murali Dhar, Newtown, PA (US); Henry H. Gu, Bordentown, NJ (US); Edwin J. Iwanowicz, Cranbury, NJ (US); Katerina Leftheris, Skillman, NJ (US); William J. Pitts, Newtown, PA (US); Timothy F. Herpin, Princeton, NJ (US); Gregory S. Bisacchi, Ringoes, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/997,963

(22) Filed: Nov. 29, 2001

(65) Prior Publication Data

US 2002/0143176 A1 Oct. 3, 2002

Related U.S. Application Data

(63) Continuation-in-part of application No. 09/428,432, filed on Oct. 27, 1999, now Pat. No. 6,399,773.
(60) Provisional application No. 60/106,186, filed on Oct. 29, 1998.

(51) Int. Cl.$^7$ .................. A61K 31/42; C07D 261/00; C07D 263/02; C07D 263/30
(52) U.S. Cl. .................. 514/374; 514/378; 548/215; 548/233; 548/240; 548/245
(58) Field of Search .................. 514/374, 378; 548/215, 233, 240, 245

(56) References Cited

U.S. PATENT DOCUMENTS

| | | | |
|---|---|---|---|
| 4,686,234 A | 8/1987 | Nelson et al. | 514/469 |
| 4,725,622 A | 2/1988 | Nelson et al. | 514/469 |
| 4,727,069 A | 2/1988 | Nelson et al. | 514/211 |
| 4,753,935 A | 6/1988 | Nelson et al. | 514/233 |
| 4,786,637 A | 11/1988 | Allison et al. | 514/233.5 |
| 4,808,592 A | 2/1989 | Nelson et al. | 514/233.5 |
| 4,861,776 A | 8/1989 | Nelson et al. | 514/233.5 |
| 4,868,153 A | 9/1989 | Allison et al. | 514/470 |
| 4,948,793 A | 8/1990 | Allison et al. | 514/233.5 |
| 4,952,579 A | 8/1990 | Nelson et al. | 514/233.5 |
| 4,959,387 A | 9/1990 | Nelson et al. | 514/469 |
| 4,992,467 A | 2/1991 | Allison et al. | 514/464 |
| 5,247,083 A | 9/1993 | Knox et al. | 544/153 |
| 5,380,879 A | 1/1995 | Sjogren | 549/310 |
| 5,444,072 A | 8/1995 | Patterson et al. | 514/320 |
| 5,665,583 A | 9/1997 | Collart et al. | 435/191 |
| 5,807,876 A * | 9/1998 | Armistead et al. | 514/374 |

FOREIGN PATENT DOCUMENTS

| | | |
|---|---|---|
| WO | WO94/01105 | 1/1994 |
| WO | WO94/12184 | 6/1994 |
| WO | WO97/40028 | 10/1997 |
| WO | WO98/40381 | 9/1998 |
| WO | WO99/55663 | 11/1999 |

OTHER PUBLICATIONS

Sheikh A. Saeed et al;" Anti–inflammatory & Anti–thrombotic effects . . . "; Med.Res.J.27,621–624(1999).*
Nature 256:331–333 (1975) Jackson et al.
J. Biol. Chem, 263: 15769–15662 (1988) Collart et al.
J. Biol. Chem. 265:5292–5295 (1990) Natsumeda et al.
J. Biol. Chem. 266:506–509 (1991) Weber.
J. Biol. Chem. 268:27286–27290 (1993) Carr.

* cited by examiner

Primary Examiner—Richard L. Raymond
Assistant Examiner—Sudhaker B. Patel
(74) Attorney, Agent, or Firm—Anastasia P. Winslow

(57) ABSTRACT

Compounds having the formula (I),

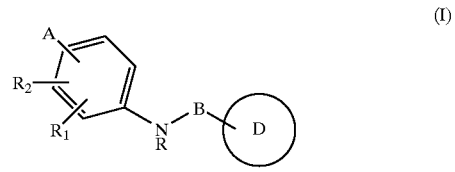

(I)

are effective as inhibitors of IMPDH enzyme and/or serine protease Factor VIIa, wherein B is a monocyclic or bicyclic carbocyclic or heterocyclic ring, D is a monocyclic or bicyclic carbocyclic or heterocyclic ring except when A is a heterocyclic ring, then D is a heterocyclic ring system, R is hydrogen or $C_{1-4}$alkyl, and A, $R_1$, $R_2$ and $R_4$ are as defined in the specification.

13 Claims, No Drawings

COMPOUNDS DERIVED FROM AN AMINE NUCLEUS AND PHARMACEUTICAL COMPOSITIONS COMPRISING SAME

RELATED APPLICATIONS

This application is a continuation-in-part of, and claims priority from, U.S. application Ser. No. 09/428,432, filed Oct. 27, 1999 now U.S. Pat. No. 6,399,773, which claims the benefit of U.S. provisional application No.60/106,186, filed Oct. 29, 1998, both of which applications are incorporated herein by reference in their entirety.

FIELD OF THE INVENTION

The invention relates to compounds that have multiple beneficial pharmacological effects, and more particularly, to aryl amine-based compounds that inhibit activity of Factor VIIa and/or IMPDH enzyme. The compounds of the present invention and pharmaceutical compositions containing them advantageously may be used as therapeutic agents for treating disorders associated with the activity of Factor VIIa and/or IMPDH.

BACKGROUND OF THE INVENTION

Inosine monophosphate dehydrogenase (IMPDH) has been shown to be a key enzyme in the regulation of cell proliferation and differentiation. IMPDH is involved in the de novo synthesis of guanosine nucleotides, which are required for cells to divide and replicate. Because B and T lymphocytes depend on the de novo pathway, inhibitors of IMPDH have been shown to possess immunosuppressive activities, as well as antineoplastic, antiviral, and antiparasitic activities. IMPDH inhibitors have been proven advantageous in mammals—e.g. the prodrug of MPA (CellCept®) and other IMPDH inhibitors are useful drugs for treating transplant rejection and autoimmune disorders, including HIV. Various other IMPDH inhibitors are in clinical studies, including Vertex compound (VX-497), and/or have been approved for use in humans. See, e.g., Compilation, *Current Medicinal Chemistry*, Vol. 6, No. 7 (July 1999), Contents: Inhibition of Inosine Monophosphate Dehydrogenase (IMPDH), at 519 ("Over 300 literature citations now address the characterization, mechanism, and biological functions of IMPDH, its role as a target for both antileukemic and immunosuppressive therapy, and its inhibition by chemotherapeutic agents.")

Coagulation factors circulating in the blood, including Factors VII, IX, X, and XI, participate in a series of reactions to produce thrombin and trigger blood coagulation. When the coagulation system is triggered (e.g., when trauma occurs), the coagulation factors are transformed into activated factors (e.g., Factors VIIa, IXa, Xa, XIa, etc.). The activated factors undergo an ordered series of reactions that ultimately lead to the conversion of Factor X to Factor Xa, which then catalyzes the conversion of prothrombin to thrombin. Thrombin is an enzyme that occupies a central position in the coagulation process. Disturbances in the natural balance between pro- and anti-coagulant forces may result in bleeding and/or thrombotic diseases. Consequently, an elevated plasma level of coagulation factors, particularly Factor VIIa, is a risk factor for fatal myocardial infarction and associated with coronary artery disease and other abnormalities of the coagulation system, e.g., thrombosis, ischemic vascular disease, intravascular clotting, stroke, embolisms, and so forth. Inhibitors of Factor VIIa may prove useful in treating these and other diseases.

As may be appreciated, those in the field of pharmaceutical research continue to seek to develop new compounds and compositions having increased effectiveness and bioavailability and/or having fewer side effects. There is particularly an interest in developing agents that can selectively and directly inhibit key enzymes and proteins having significant biolological effects such as IMPDH and Factor VIIa. The compounds of this invention are useful as inhibitors of IMPDH and/or Factor VIIa, and thus may have multiple beneficial pharmacological properties.

SUMMARY OF THE INVENTION

The present invention provides compounds of the following formulae (I), their enantiomers, diastereomers, tautomers and pharmaceutically acceptable salts, prodrugs and solvates thereof:

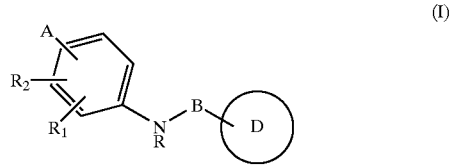

(I)

wherein:
D is a monocyclic or bicyclic ring system optionally containing up to 4 heteroatoms selected from N, O, and S, and wherein a $CH_2$ adjacent to any of said N, O or S heteroatoms is optionally substituted with oxo (=O), and wherein D is optionally substituted by one to four $(CR^9R^{10})_n E$ groups;

A is $R^3$ or $R^4$, provided that if A is $R_3$, then D is a monocyclic or bicyclic heterocyclic ring system wherein a $CH_2$ adjacent to any of N, O or S heteroatoms in said ring is optionally substituted with oxo (=O), and wherein D is optionally substituted by one to four $(CR^9R^{10})_n E$ groups;

$R^3$ is a 5- or 6-membered saturated or unsaturated heterocyclic ring system containing up to 4 heteroatoms selected from N, O, and S, said heterocyclic ring system being optionally substituted with 0–3 $R^5$, wherein when $R^5$ is hydroxy, the heterocycle may undergo tautomerization to an oxo species, or exist as an equilibrium mixture of both tautomers;

$R^4$ is selected from H, halogen, $NO_2$, $CF_3$, $C_0$–$C_4$ alkylCN, $C_1$–$C_4$alkoxy-, $C_0$–$C_4$ alkylhydroxy, $C_1$–$C_4$ alkyl-, $C_1$–$C_4$ alkylcarbonyl-, $C_0$–$C_4$ alkylOCOR$^6$, $C_0$–$C_4$ alkylOC(=O)OR$^6$, $C_0$–$C_4$ alkylOC(=O)NR$^6$R$^7$, $C_0$–$C_4$ alkylNR$^6$R$^7$, $C_0$–$C_4$ alkylNR$^7$C(=O)OR$^6$, $C_0$–$C_4$ alkylNR$^6$SO$_2$NR$^6$R$^7$, $C_0$–$C_4$ alkylNR$^7$SO$_2$R$^6$, $C_0$–$C_4$ alkylSR$^6$, $C_0$–$C_4$ alkylS(O)R$^6$, $C_0$–$C_4$ alkylSO$_2$R$^6$, SO$_3$R$^7$, $C_0$–$C_4$ alkylSO$_2$NR$^6$R$^7$, $C_0$–$C_4$alkyl SO$_2$NR$^7$ CO$(CR^9R^{10})_q R^6$, $C_0$–$C_4$ alkylCO$_2$R$^6$, $C_0$–$C_4$ alkylCONR$^6$R$^7$, and $C_0$–$C_4$CONR$^7$SO$_2$$(CR^9R^{10})_q R^6$;

$R^5$ is selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, OH, oxo, $C_1$–$C_4$alkoxy, $C_1$–$C_4$alkylcarbonyl, CN, NR$^6$R$^7$, SR$^7$, S(O)R$^7$, SO$_2$R$^7$, SO$_3$R$^7$, SO$_2$NR$^6$, CO$_2$R$^6$, and CONR$^6$R$^7$;

R is H or $C_1$–$C_4$alkyl;

$R^1$ and $R^2$ are each independently selected from H, halogen, $NO_2$, $C_1$–$C_4$alkyl, $C_3$–$C_{10}$cycloalkyl, $C_2$–$C_6$alkenyl, $C_2$–$C_6$alkynyl, haloalkyl, haloalkoxy, OR$^6$, O$(CR^9R^{10})_r$CO$_2$R$^6$, O$(CR^9R^{10})_m$NR$^6$R$^7$, O$(CR^9R^{10})_p$CN, O$(CR^9R^{10})_r$C(=O)NR$^6$R$^7$, $C_1$–$C_4$alkylcarbonyl-, CN, NR$^6$R$^7$, NR$^7$(CR$^9$ $R^{10})_rCO_2R^6$, $NR^7OR^6$, $NR^7(CR^9R^{10})_mOR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_mOR^6$, $NR^7(CR^9R^{10})_mNR^6R^7$, $NR^7(CR^9R^{10})_mSO_2(CR^9R^{10})_qR^6$, $SR^7$, $S(O)R^7$, $SO_2R^7$, $SO_2NR^6$, $SO_3R^7$, $CO_2R^6$, and $CONR^6R^7$; or, alternatively, $R^1$ and $R^2$, when on adjacent carbon atoms, may be taken together to be methylenedioxy or ethylenedioxy;

$R^6$, $R^7$ and $R^8$ are each independently selected from H, $C_1$–$C_6$alkyl, $C_3$–$C_{10}$ cycloalkyl, $C_2$–$C_6$alkenyl, $C_2$–$C_6$alkynyl, $C_1$–$C_6$ alkylcarbonyl, $C_3$–$C_7$ cycloalkyl($C_0$–$C_5$ alkyl)carbonyl, $C_1$–$C_6$ alkoxycarbonyl, aryl($C_0$–$C_5$alkyl)carbonyl, aryl($C_1$–$C_5$ alkoxy)carbonyl, heterocyclic($C_0$–$C_5$ alkyl)carbonyl, heterocyclic($C_1$–$C_5$ alkoxy)carbonyl, $C_1$–$C_6$alkylsulfonyl, arylsulfonyl, heteroarylsulfonyl, $C_0$–$C_4$alkylaryl, $C_0$–$C_4$alkylheterocyclic, wherein said cycloalkyl, aryl or heterocyclic groups are substituted with 0–2 substituents independently selected from the group consisting of $C_1$–$C_4$alkyl, hydroxy, $C_1$–$C_4$ alkoxy, F, Cl, Br, haloalkyl, $NO_2$ and CN;

or, alternatively, $R^6$ and $R^7$, or $R^6$ and $R^8$, or $R^7$ and $R^8$, when both substituents are on the same nitrogen atom [as in ($-NR^6R^7$) or ($-NR^7R^8$)], can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, said heterocycle being optionally substituted with 0–3 groups selected from oxo, $C_0$–$C_4$alkylOH, $C_0$–$C_4$alkylO$C_1$–$C_4$alkyl, $C_0$–$C_4$alkylCONH$_2$, $C_0$–$C_4$alkylCO$_2$C$_0$–$C_4$alkyl, $C_1$–$C_6$alkyl, $C_1$–$C_4$ alkoxy, $C_3$–$C_7$ cycloalkyl, —$C_0$–$C_6$ alkylcarbonyl, $C_3$–$C_7$ cycloalkylcarbonyl, $C_1$–$C_6$ alkoxycarbonyl, $C_3$–$C_7$ cycloalkoxycarbonyl, —NHCOalkyl, aryl, heteroaryl, arylalkoxycarbonyl, heteroarylalkoxycarbonyl, $C_1$–$C_6$ alkylsulfonyl, arylsulfonyl and heteroarylsulfonyl;

B is a monocyclic or bicyclic ring system optionally containing up to 4 heteroatoms selected from N, O, and S, and wherein a $CH_2$ adjacent to any of said N, O or S heteroatoms is optionally substituted with oxo ($=O$), and wherein B is optionally substituted by one to four $R^{11}$ groups;

$R^9$ is H or $C_1$–$C_4$alkyl;

$R^{10}$ is selected from H or $C_1$–$C_4$ alkyl, $C_1$–$C_4$ alkylhydroxy, $C_1$–$C_4$alkylaryl or $C_1$–$C_4$alkylheteroaryl, wherein said aryl or heteroaryl group may be substituted with 0 –3 groups independently selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, OH, $C_1$–$C_4$alkoxy, $C_1$–$C_4$alkylcarbonyl, CN, $NR^6R^7$, $SR^6$, $S(O)R^6$, $SO_2R^6$, $SO_3R^6$, $SO_2NR^6$, $CO_2R^6$, and $CONR^6R^7$;

$R^{11}$ is selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, $C_1$–$C_4$alkoxy-, $OR^6$, $O(CR^9R^{10})_rCO_2R^6$, $O(CR^9R^{10})_mNR^6R^7$, $O(CR^9R^{10})_pCN$, $O(CR^9R^{10})_rC(=O)NR^6R^7$, $C_1$–$C_4$alkylcarbonyl-, CN, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_mOR^6$, $NR^7(CR^9R^{10})_mNR^6R^7$, $NR^7(CR^9R^{10})_mSO_2(CR^9R^{10})_qR^6$, $SR^7$, $S(O)R^7$, $SO_2R^7$, $SO_2NR^6$, $SO_3R^7$, $CO_2R^6$, and $CONR^6R^7$;

E is selected from H, halogen, $NO_2$, $C_1$–$C_4$alkyl, $C_3$–$C_{10}$ cycloalkyl, $C_2$–$C_6$ alkenyl, $C_2$–$C_6$ alkynyl, haloalkyl, haloalkoxy, $OR^6$, CN, CHO, $CO_2R^6$, $CONR^6R^7$, $OCOR^6$, $OC(=O)OR^6$, $OC(=O)NR^6R^7$, $OCH_2CO_2R^6$, $C(=O)R^6$, $NR^6R^7$, $NR^7C(=O)R^6$, $NR^7C(=O)OR^6$, $NR^7C(=O)C(=O)OR^6$, $NR^7C(=O)C(=O)NR^6R^7$, $NR^7C(=O)C(=O)(C_1$–$C_6$alkyl), $NR^7C(=NCN)OR^6$, $NR^7C(=O)NR^6R^7$, $NR^7C(=NCN)NR^6R^7$, $NR^7C(=NR^6)NR^7R^8$, $NR^6SO_2NR^6R^7$, $NR^7SO_2R^6$, $SR^6$, $S(=O)R^6$, $SO_2R^6$, $SO_3R^7$, $SO_2NR^6R^7$, $NHOR^6$, $NR^6NR^7NR^8$, $N(COR^6)OH$, $N(CO_2R^6)OH$, $CO_2R^6$, $CONR^7(CR^9R^{10})_rR^6$, $CO(CR^9R^{10})_pO(CHR^9)_qCO_2R^6$, $CO(CR^9CR^{10})_rOR^6$, $CO(CR^9R^{10})_pO(CR^9R^{10})_qR^6$, $CO(CR^9CR^{10})_rNR^6R^7$, $OC(O)O(CR^9R^{10})_mNR^6R^7$, $O(CO)N(CR^9R^{10})_rR^6$, $O(CR^9R^{10})_mNR^6R^7$, $NR^7C(O)(CR^9R^{10})_rR^6$, $NR^7C(O)(CR^9R^{10})_rOR^6$, $NR^7C(=NC)(CR^9R^{10})_rR^6$, $NR^7CO(CR^9R^{10})_rNR^6$, $R^7$, $NR^7(CR^9R^{10})_mOR^6$, $NR^7(CR^9R^{10})_r CO_2R^6$, $NR^7(CR^9R^{10})_mNR^6R^7$, $NR^7(CR^9R^{10})_nSO_2(CR^9R^{10})_qR^6$, $CONR^7(CR^9R^{10})_nSO_2(CR^9R^{10})_qR^6$, $SO_2NR^7(CR^9R^{10})_n$, $CO(CR^9R^{10})_qR^6$, $SO_2NR^6(CR^9R^{10})_mOR^6$, $C_3$–$C_{10}$ cycloalkylmethyl, aryl, heterocyclic and alkylaryl, wherein said aryl groups may be substituted with 0–2 substituents independently selected from $R^{12}$;

$R^{12}$ at each occurrence is independently selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, oxo, $OR^6$, $O(CR^9R^{10})_rCO_2R^6$, $O(CR^9R^{10})_mNR^6R^7$, $O(CR^9R^{10})_pCN$, $O(CR^9R^{10})_rC(=O)NR^6R^7$, $C_1$–$C_4$alkylcarbonyl-, CN, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_mOR^6$, $NR^7(CR^9R^{10})_mNR^6R^7$, $NR^7(CR^9R^{10})_mSO_2(CR^9R^{10})_qR^6$, $SR^7$, $S(O)R^7$, $SO_2R^7$, $SO_2NR^6$, $SO_3R^7$, $CO_2R^6$, and $CONR^6R^7$;

n is an integer having a value from 0–4;

m is an integer having a value from 2–6;

p is an integer having a value from 1–3;

q is an integer having a value from 0–3; and r is an integer having a value from 0–6.

The present invention also provides pharmaceutical compositions comprising the compounds of formula (I) and methods of treating IMPDH-associated and/or Factor VIIa-associated disorders using the compounds of formula I.

DETAILED DESCRIPTION OF THE INVENTION

Listed below are definitions of various terms used in the specification and claims to describe the present invention.

The term "alkyl" refers to straight or branched chain alkyl.

The term "$C_{integer}$–$C_{integer}$" refers to a variable number of carbon atoms in a group depending on the integer values, as in $C_0$–$C_4$alkyl, which is meant to indicate a straight or branched alkyl group containing 0–4 carbon atoms. A group with 0 (zero) carbon atoms indicates that the carbon atom is absent, i.e. there is a direct bond connecting adjacent groups. For example, the term "$C_0$–$C_4$ alkylhydroxy" includes hydroxy as well as alkyl groups having one to four carbon atoms substituted by hydroxy.

Similarly, D is defined as a ring which may be substituted with the group "$(CR^9R^{10})_nE$" and the subscript n may be 0. This is meant to indicate that the group E may be directly connected to D by a bond, i.e. D–E.

The term "halogen" or "halo" refers to fluorine, chlorine, bromine or iodine.

The term "aryl" refers to monocyclic or bicyclic aromatic hydrocarbons having 6 to 12 carbon atoms in the ring portion, such as phenyl, naphthyl, and biphenyl groups which may be optionally substituted.

The term "alkenyl" refers to straight or branched chain alkenyl groups.

The term "alkynyl" refers to straight or branched chain alkynyl.

The term "cycloalkyl" refers to an optionally substituted, saturated cyclic hydrocarbon ring system.

The term "saturated" means partially or fully saturated, unless otherwise indicated.

The term "carbocyclic" refers to an optionally substituted, fully saturated or unsaturated, aromatic or nonaromatic cyclic group, which is a 3 to 7 membered monocyclic, or a 7 to 11 membered bicyclic group, and all the atoms in the ring are carbon atoms. Exemplary groups include phenyl, naphthyl, anthracenyl, cyclohexyl, cyclohexenyl, and the like.

The terms "heterocycle" and "heterocyclic" refer to an optionally substituted, fully saturated or unsaturated, aromatic or nonaromatic cyclic group, which is a 3 to 7 membered monocyclic, or a 7 to 11 membered bicyclic group, which has at least one heteroatom in at least one carbon-containing ring. Each heterocyclic ring may contain 1, 2, 3, or 4 heteroatoms selected from nitrogen, oxygen and sulfur, where the nitrogen and sulfur heteroatoms may also optionally be oxidized and the nitrogen heteroatoms may also optionally be quaternized. The heterocyclic group may be attached via a nitrogen or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydrothiopyranyl, tetrahydropyranyl, morpholinyl, thiamorpholinyl, thiamorpholinyl sulfoxide, tetrahydrothiopyranylsulfone, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

As used herein the term "treating" includes prophylactic and therapeutic uses, and refers to the alleviation of symptoms of a particular disorder in a patient, the improvement in symptoms or conditions associated with a particular disorder, or the prevention of a particular physiological response, such as an immune response (as with transplant rejection). The term "patient" refers to a mammal, preferably a human.

The compounds of this invention may contain one or more asymmetric carbon atoms and thus may occur as racemates and racemic mixtures, single enantiomers, diastereomeric mixtures and individual diastereomers. All such isomers of the compounds disclosed herein are expressly included within the scope of the present invention. Each stereogenic carbon may be of the R or S configuration.

One skilled in the field can select substituents and variables thereof that result in stable compounds, which are contemplated within the present invention. The term "stable" as used herein refers to compounds which possess sufficient stability to allow for their manufacture and which maintain their integrity for a sufficient period of time to be useful as therapeutic or diagnostic agents.

As used herein, the compounds of this invention are defined to include pharmaceutically acceptable derivatives and prodrugs thereof. A "pharmaceutically acceptable derivative or prodrug" includes any pharmaceutically acceptable salt, ester, salt of an ester, or other derivative of a compound of the present invention which, upon administration to a subject, is capable of providing (directly or indirectly) a compound of the invention. Particularly favored derivatives and prodrugs are those that increase the bioavailability of the compounds of the present invention when such compound is administered to a subject (e.g., by allowing an orally administered compound to be more readily absorbed into the blood) or which enhance delivery of the parent compound to a biological compartment (e.g., the brain or lymphatic system). Preferred prodrugs include derivatives where a group that enhances aqueous solubility or active transport through the gut membrane is appended to a compound of the present invention.

Pharmaceutically acceptable salts of the compounds disclosed herein include those derived from pharmaceutically acceptable inorganic and organic acids and bases known to those skilled in the art. Examples of suitable acid salts include, but are not limited to, the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, filmarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, trifluoroacetic, tosylate and undecanoate. Other acids, for example oxalic, while not in themselves pharmaceutically acceptable, may be employed in the preparation of salts useful as intermediates in obtaining the compounds of the present invention and are contemplated as within the scope of the invention.

Salts derived from appropriate bases include, but are not limited to, the following: alkali metal (e.g., sodium), alkaline earth metal (e.g., magnesium), ammonium and N-($C_{1-4}$ alkyl)$_4^+$ salts. The present invention also envisions the quaternization of any basic nitrogen-containing groups of the compounds disclosed herein. Water- or oil-soluble or dispersible products may be obtained by such quaternization.

Preferred Compounds

Preferred compounds according to the invention are those having the formulae (Ia) or (Ib),

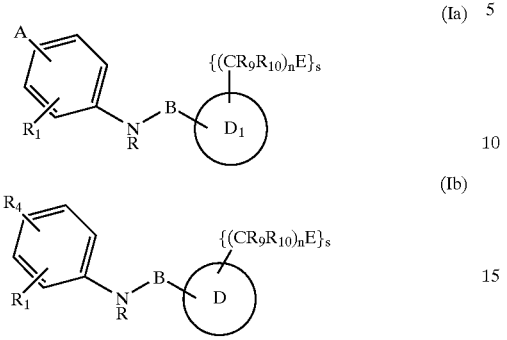

and/or pharmaceutically-acceptable salts, hydrates or pro-drugs thereof, wherein:

A is $R^3$ or $R^4$;

B is a monocyclic or bicyclic ring system substituted with one to two $R^{11}$ groups;

D is a monocyclic or bicyclic heterocyclic or carbocyclic ring system;

$D_1$ is a monocyclic or bicyclic heterocyclic ring system;

$R^3$ is selected from a 5 or 6 membered saturated or fully or partially unsaturated heterocyclic ring, including without limitation oxazolyl, thiazolyl, thiadiazolyl, oxadiazolyl, tetrazolyl, triazolyl, diazolyl, and pyrazolyl, said $R^3$ group being optionally substituted with one to two groups selected from hydrogen, halogen, $NO_2$, $C_1$–$C_4$alkyl, haloalkyl, haloalkoxy, OH, oxo, $C_1$–$C_4$alkoxy, $C_1$–$C_4$alkylcarbonyl, CN, $NH_2$, $NH(C_{1-4}alkyl)$, and $N(alkyl)_2$;

$R^4$ is selected from H, halogen, $NO_2$, $CF_3$, $C_0$–$C_4$ alkylCN, $C_1$–$C_4$alkoxy-, $C_0$–$C_4$ alkylhydroxy, $C_1$–$C_4$ alkyl-, $C_1$–$C_4$ alkylcarbonyl-, $C_0$–$C_4$alkylOCOR$^6$, $C_0$–$C_4$ alkylNR$^6$R$^7$, $C_0$–$C_4$ alkylNR$^7$C($=$O)OR$^6$, $C_0$–$C_4$ alkylCO$_2$R$^6$, and $C_0$–$C_4$ alkylCONR$^6$R$^7$;

R is H or $C_1$–$C_4$alkyl;

$R^9$ and $R^{10}$ are selected from H and $C_1$–$C_4$ alkyl;

$R^1$ is hydrogen, halogen, $NO_2$, $C_1$–$C_4$alkyl, $C_3$–$C_7$cycloalkyl, $C_2$–$C_6$alkenyl, haloalkyl, haloalkoxy, $OR^6$, CN, $NR^6R^7$, $NR^7C(=O)R^6$, $CO_2R^6$, or $CONR^6R^7$;

E is selected from hydrogen, halogen, $NO_2$, $C_1$–$C_4$alkyl, $C_3$–$C_7$cycloalkyl, $C_2$–$C_6$ alkenyl, haloalkyl, haloalkoxy, $OR^6$, CN, $CO_2R^6$, $CONR^6R^7$, $OCH_2CO_2R^6$, $C(=O)R^6$, $NR^6R^7$, $NR^7C(=O)R^6$, $NR^7C(=O)NR^6R^7$, $NR^6SO_2NR^6R^7$, $NR^7SO_2R^6$, $NHOR^6$, $NR^7C(O)(CR^9R^{10})_rR^6$, $NR^7C(O)(CR^9R^{10})_r OR^6$, $NR^7CO(CR^9R^{10})_rNR^6R^7$, $NR^7(CR^9R^{10})_m OR^6$, $NR^7(CR^9R^{10})_rCO_2R^6$, $NR^7(CR^9R^{10})_mNR^6R^7$, $C_3$–$C_7$cycloalkylmethyl, aryl, heterocyclic and $C_1$–$C_4$alkylaryl;

$R^6$ and $R^7$ are each independently selected from H, $C_1$–$C_4$alkyl, $C_3$–$C_7$cycloalkyl, $C_2$–$C_6$alkenyl, $C_1$–$C_4$alkylcarbonyl, $C_3$–$C_7$cycloalkyl($C_0$–$C_5$ alkyl)carbonyl, $C_1$–$C_4$alkoxycarbonyl, aryl($C_0$–$C_4$alkyl) carbonyl, aryl($C_1$–$C_4$ alkoxy)carbonyl, heterocyclic ($C_0$–$C_4$alkyl)carbonyl, heterocyclic($C_1$–$C_4$ alkoxy) carbonyl, $C_0$–$C_4$alkylaryl, $C_0$–$C_4$alkylheterocyclic, wherein said cycloalkyl, aryl or heterocyclic groups are substituted with 0–2 substituents independently selected from $C_1$–$C_4$alkyl, hydroxy, $C_1$–$C_4$ alkoxy, F, Cl, Br, haloalkyl, $NO_2$ and CN;

or, alternatively, $R^6$ and $R^7$ taken together with the nitrogen atom to which they are attached form a heterocycle selected from 1-piperidinyl, 1-morpholinyl, 1-pyrrolidinyl, thiamorpholinyl, thiazolidinyl, 1-piperazinyl, 1-imidazolyl, and 1-tetrazolyl, said heterocycle being optionally substituted with 0–2 groups selected from oxo, $C_0$–$C_4$alkylOH, $C_0$–$C_4$alkylOC$_1$–$C_4$alkyl, $C_0$–$C_4$alkylCONH$_2$, $C_0$–$C_4$alkylCO$_2$C$_1$–$C_4$alkyl, $C_1$–$C_6$alkyl, $C_1$–$C_4$ alkoxy, $C_3$–$C_7$cycloalkyl, —$C_0$–$C_4$alkylcarbonyl, $C_1$–$C_6$ alkoxycarbonyl, —NHCOalkyl, aryl, and heteroaryl;

$R^{11}$ is selected from H, halogen, $NO_2$, $C_1$–$C_4$alkyl, $C_3$–$C_{10}$ cycloalkyl, $C_2$–$C_6$alkenyl, $C_2$–$C_6$alkynyl, haloalkyl, haloalkoxy, $OR^6$, $O(CR^9R^{10})_rCO_2R^6$, $O(CR^9R^{10})_mNR^6R^7$, $O(CR^9R^{10})_pCN$, $O(CR^9R^{10})_rC(=O)NR^6R^7$, $C_1$–$C_4$alkylcarbonyl-, CN, $NR^6R^7$, $NR^7(CR^9R^{10})_rCO_2R^6$, $NR^7OR^6$, $NR^7(CR^9R^{10})_m OR^6$, $NR^7CH[(CR^9R^{10})_pOR^6]_2$, $NR^7C[(CR^9R^{10})_pOR^6]_3$, $NR^7C(=O)R^6$, $NR^7(CR^9R^{10})_m OR^6$, $NR^7(CR^9 R^{10})_m NR^6R^7$, $NR^7(CR^9R^{10})_m SO_2(CR^9R^{10})_q R^6$, $SR^7$, $S(O)R^7$, $SO_2R^7$, $SO_2NR^6$, $SO_3R^7$, $CO_2R^6$, and $CONR^6R^7$;

m is an integer having a value from 2–4;

n is an integer having a value from 0–4;

r is an integer having a value from 0–4; and s is an integer having a value of 0 to 2.

In compounds of formula (I), preferred ring systems for "B" are selected from:

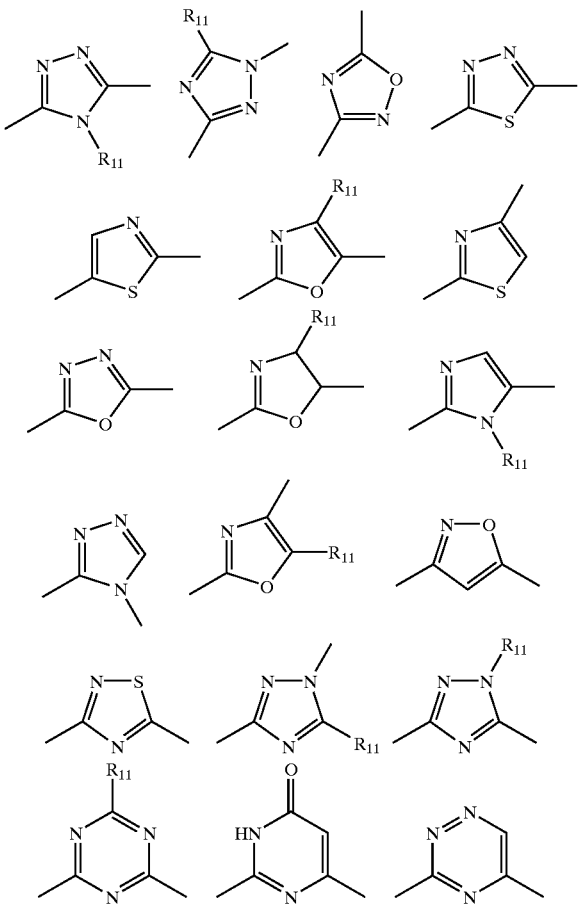

-continued

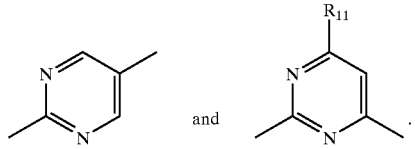 and

More preferred are compounds according to formula (Ic), or pharmaceutically-acceptable salts, hydrates or prodrugs thereof,

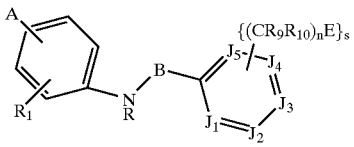

(Ic)

in which each of A, R$^1$, R, B, E, R$^9$ and R$^{10}$ are defined as above;

J$^1$, J$^2$, J$^3$, J$^4$, and J$^5$ are selected from carbon and nitrogen, provided that no more than four of J$^1$, J$^2$, J$^3$, J$^4$, and J$^5$ are nitrogen;

the group or groups (CR$^9$R$^{10}$)$_n$E are attached to any one or more of J$^1$, J$^2$, J$^3$, J$^4$, and J$^5$ that are carbon atoms; and s is 1 or 2.

Even more preferred are compounds according to formula (Id), or pharmaceutically-acceptable salts, hydrates or prodrugs thereof,

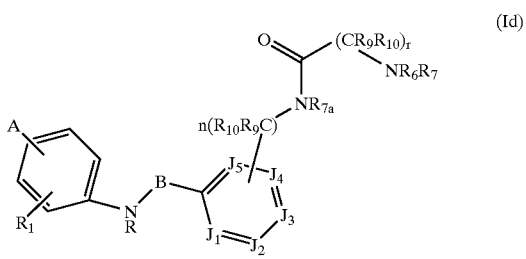

(Id)

in which

A, R$^1$, R, B, J$^1$, J$^2$, J$^3$, J$^4$, and J$^5$ are defined as immediately above for compounds of formula (Ic);

R$^{7a}$ selected from H, C$_1$–C$_4$alkyl, and C$_3$–C$_7$cycloalkyl;

R$^9$ and R$^{10}$ are selected from H and C$_1$–C$_4$alkyl;

n and r are selected from 0, 1, 2, 3, or 4; and

R$^6$ and R$^7$ are each independently selected from H, C$_1$–C$_4$alkyl, C$_3$–C$_7$cycloalkyl, C$_2$–C$_6$alkenyl, C$_1$–C$_4$alkylcarbonyl, C$_3$–C$_7$cycloalkyl(C$_0$–C$_5$ alkyl)carbonyl, C$_1$–C$_4$alkoxycarbonyl, aryl(C$_0$–C$_4$alkyl)carbonyl, aryl(C$_1$–C$_4$ alkoxy)carbonyl, heterocyclic (C$_0$–C$_4$alkyl)carbonyl, heterocyclic(C$_1$–C$_4$ alkoxy)carbonyl, C$_0$–C$_4$alkylaryl, C$_0$–C$_4$alkylheterocyclic, wherein said cycloalkyl, aryl or heterocyclic groups are substituted with 0–2 substituents independently selected from C$_1$–C$_4$alkyl, hydroxy, C$_1$–C$_4$ alkoxy, F, Cl, Br, haloalkyl, NO$_2$ and CN;

or, alternatively, R$^6$ and R$^7$ taken together with the nitrogen atom to which they are attached form a heterocycle selected from 1-piperidinyl, 1-morpholinyl, 1-pyrrolidinyl, thiamorpholinyl, thiazolidinyl, 1-piperazinyl, 1-imidazolyl, and 1-tetrazolyl, said heterocycle being optionally substituted with 0–2 groups selected from oxo, C$_0$–C$_4$alkylOH, C$_0$–C$_4$alkylOC$_1$–C$_4$alkyl, C$_0$–C$_4$alkylCONH$_2$, C$_0$–C$_4$alkylCO$_2$C$_1$–C$_4$alkyl, C$_1$–C$_6$alkyl, C$_1$–C$_4$ alkoxy, C$_3$–C$_7$cycloalkyl, —C$_0$–C$_4$alkylcarbonyl, C$_1$–C$_6$ alkoxycarbonyl, —NHCOalkyl, aryl, and heteroaryl.

Methods of Preparation

The compounds of the present invention may be synthesized using conventional techniques known in the art. Advantageously, these compounds are conveniently synthesized from readily available starting materials. Additionally, illustrative general synthetic schemes for making compounds of the present invention are set forth below. The various steps in the synthesis may be performed in an alternate order to give the desired compound(s). The groups A, D, R$_1$, R$_6$, R$_7$, in the synthetic schemes below are intended to designate the groups as recited in the claims. The group X in the schemes refers to halogen, unless otherwise indicated.

The preparation of heterocycles useful to this invention is described in the literature, e.g., Katritzky et al, "Comprehensive Heterocyclic Chemistry, The Structure, Reactions, Synthesis and Uses of Heterocyclic Compounds," (Pergamon Press New York, 1984 [1$^{st}$ ed.], and 1996).

Scheme 1

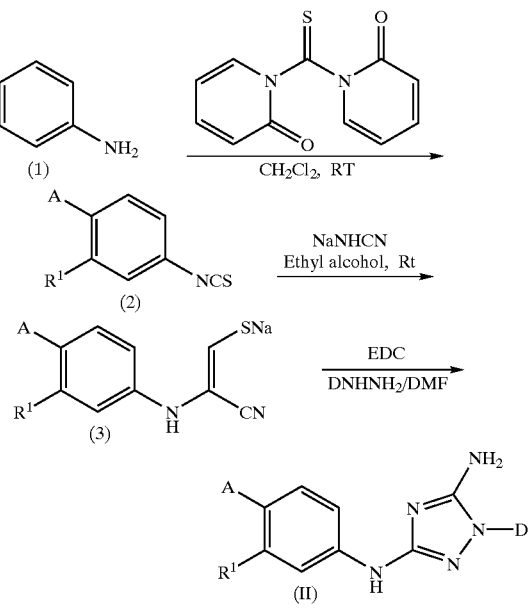

Reaction of an appropriately-substituted amine (1) with a reagent such as 1,1'-thiocarbonyldi-2(1H)-pyridone,1,1'-thiocarbonyldiimidazole or thiophosgene in a solvent such as methylene chloride or dioxane yields the isothiocyanate (2). Treatment of the isothiocyanate (2) with sodium salt of cyanamide yields the sodium salt of N-cyanothiourea (3), which is cyclized to the substituted 1,2,4-aminotriazole (II), using an appropriately-substituted hydrazine and a dehydrating agent such as EDC or DCC.

Scheme 2

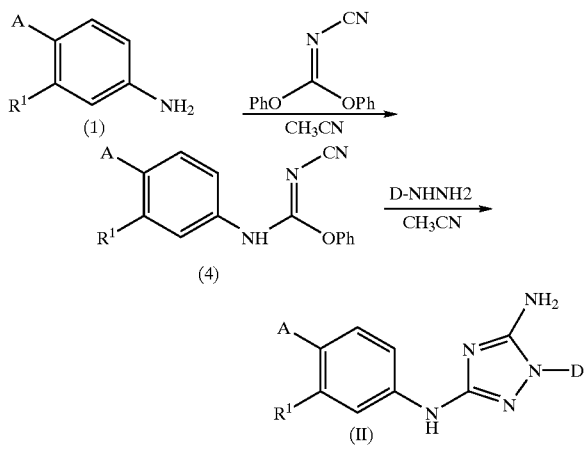

An appropriately-substituted amine (1) can be reacted with diphenyl cyanocarbonimidate to yield the N-cyano-O-phenylisourea (4). Cyclization of compound (4) to the substituted triazole (II) is achieved using an appropriately-substituted hydrazine and a solvent such as acetonitrile.

Scheme 3

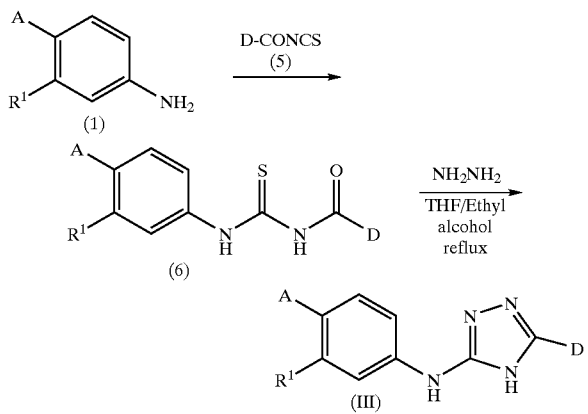

Acylisothiocyanates (5) are useful intermediates in the production of some compounds of this invention. Compounds (5) are commercially available or can be readily prepared by reaction of an acid chloride with sodium or potassium isothiocyanate in an inert solvent such as dioxane. Acid chlorides are either commercially available or can be readily prepared by reaction of a carboxylic acid and a reagent such as thionyl chloride, or oxalyl chloride in the presence of a catalytic amount of DMF, in an inert solvent such as chloroform or methylene chloride. Reaction of an appropriately-substituted amine (1) with an acylisothiocyanate (5) yields the thiourea (6). The thiourea (6) is cyclized to (III) using hydrazine in a solvent such as EtOH or a solvent mixture such as THF and EtOH, at a temperature preferably between 60° C. and the boiling point of the solvent(s) utilized.

Scheme 4

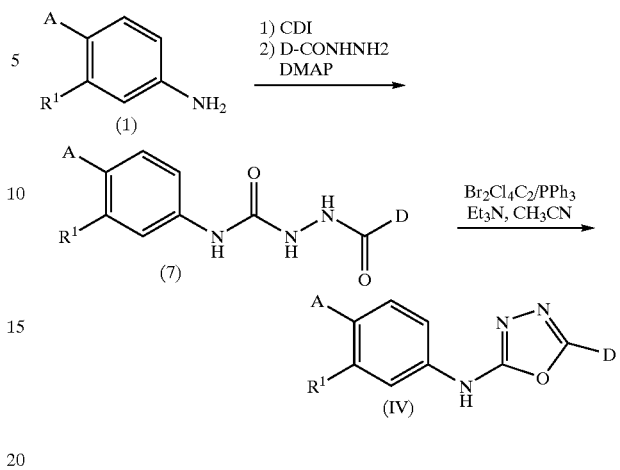

Reaction of an appropriately-substituted amine (1) with an activating agent such as 1,1' carbonyldiimidazole followed by treatment with an appropriately-substituted hydrazine yields the carbonylhydrazide (7). The carbonylhydrazide (7) on treatment with 1,2-dibromotetrachloroethane and triphenylphosphine in the presence of a suitable base such as TEA and an appropriate solvent such as acetonitrile yields compound (IV).

Scheme 5

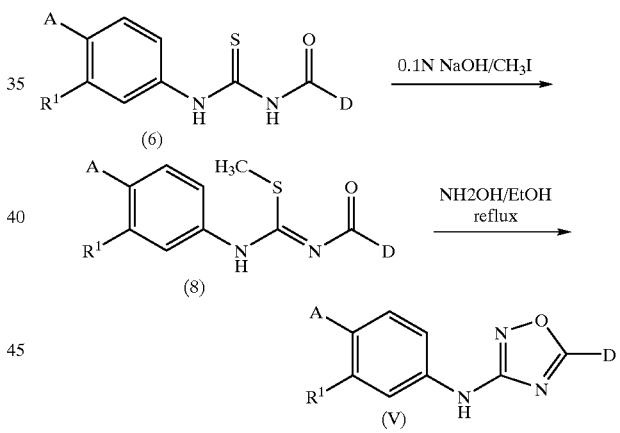

Reaction of thiourea (6) (see Scheme 3), with a base such as sodium hydroxide or sodium hydride followed by an alkylating agent such as methyl iodide gives the S-methylisothiocarbamoyl intermediate (8). Treatment of (8) with hydroxylamine in the presence of a suitable solvent such as EtOH or bu-OH at a temperature preferably between 60° C. and 110° C. results in cyclization to the desired 3-amino-1,2,4-oxadiazole (V).

Scheme 6

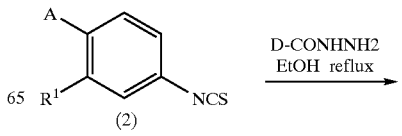

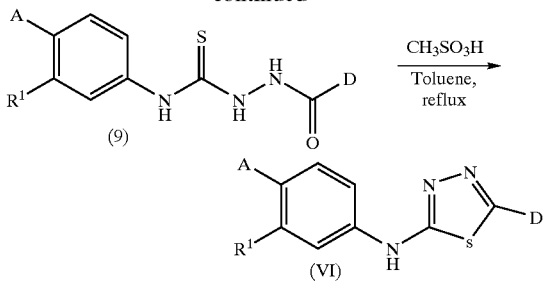

Reaction of acyl isothiocyene with D-CONHNH$_2$ in EtOH yields thiourea (9). Thiourea can be cyclized to the desired heterocycle (VI) using a dehydrating agent such as methanesulphonic acid, in an inert solvent such as toluene or xylene, at a temperature preferably between 80° C. to 140° C.

Scheme 7

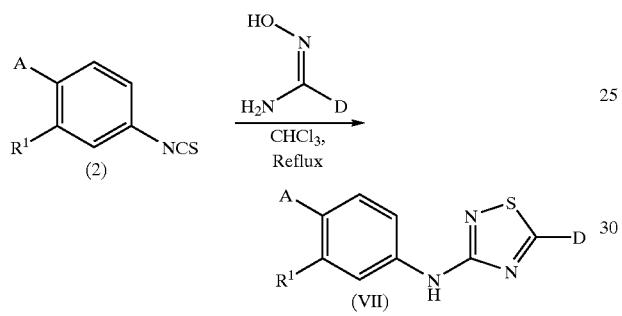

Reaction of an appropriately-substituted isothiocyanate (2) (see Scheme 1) and an amidoxime in a solvent, such as chloroform or toluene, at a temperature preferably between 60° C. and 110° C. results in the production of the desired heterocycle (VII). Amidoximes useful to this invention are either commercially available or can be readily prepared by methods known to one skilled in the art. One such method involves reaction of a nitrile with anhydrous hydrochloric acid in anhydrous MeOH followed by reaction of the resulting imidate with hydroxylamine.

Scheme 8

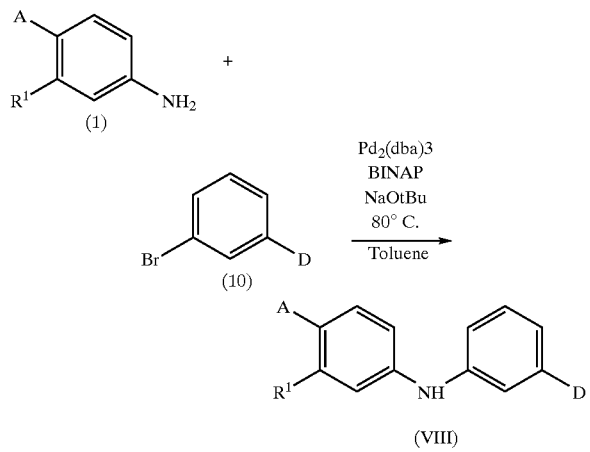

The coupling of amines with haloaryl compounds has been described in the literature, e.g., in "Rational Develop- ment of Practical Catalysts for Aromatic Carbon-Nitrogen Bond Formation," *Accounts of Chemical Research*, Vol. 31 (1998), at pp. 805–818. Reaction of an appropriately-substituted aniline (1) with an appropriately-substituted haloaryl compound (10) in the presence of a catalyst such as tris(dibenzylideneacetone)dipalladium, a ligand such as BINAP, a base such as sodium tert-butoxide, and a solvent such as toluene or dioxane, preferably at a temperature between 80–110° C., results in production of the desired diarylamines (VIII).

Bromo- or iodo-aryl intermediates such as 3-bromobiphenyl are commercially available or may be readily prepared by methods known to one skilled in the art. One such method involves bromination of the aryl ring with Br$_2$ in the presence of iron. See also Carey et al., "Advanced Organic Chemistry," at Chap. 11 (3$^{rd}$ edition, Plenum Press New York, 1990).

Scheme 9

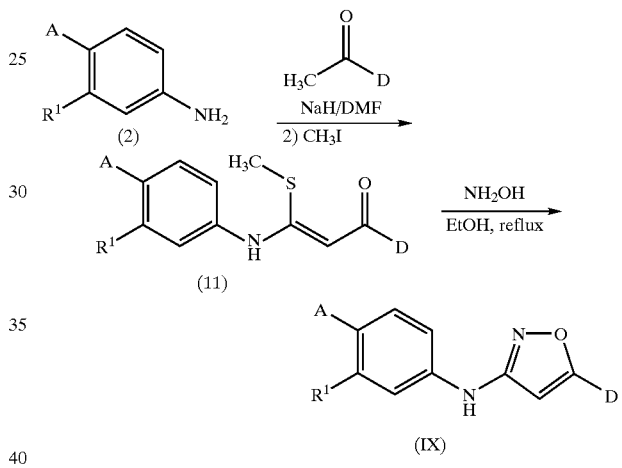

Reaction of an appropriately-substituted isocyanate (2) with a ketone in the presence of a base such as sodium hydride and an alkylating agent such as methyl iodide gives a thiomethyl intermediate (11). Treatment of the intermediate (11) with hydroxylamine in a solvent such as ethyl or butyl alcohol at a temperature preferably between 60–120° C. yields the appropriately-substituted 3-aminoisoxazoles (IX). Ketones useful to this invention are either commercially available or can be readily prepared by several methods, such as Friedel-Crafts acylation (see Carey, supra); or by hydrolysis of an enol ether or oxidation of an alcohol (see Larock et al., "Comprehensive Organic Transformations, A Guide to Functional Group Preparations" [VCH Publishers, New York, 1989]).

Scheme 10

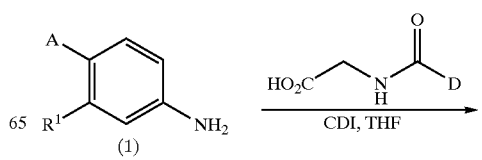

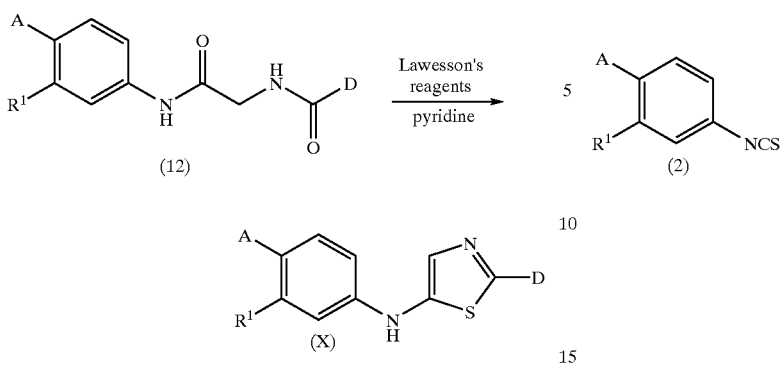

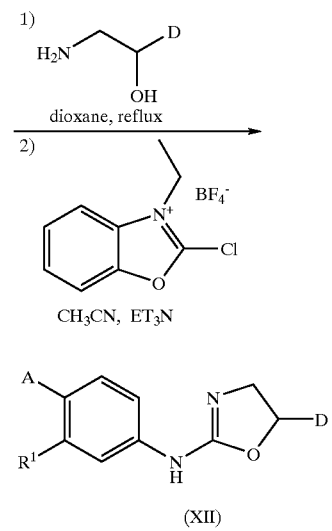

Reaction of an amine (1) with an amino acid in the presence of an activating agent such as 1,1'-carbonyldiimidazole in a suitable solvent such as THF yields amide (12). Amides also may be readily prepared by a number of methods including reaction of an amine with an acid chloride, or coupling of a carboxylic acid and the amine in the presence of a variety of coupling agents such as EDC or DCI, in the presence of an amine base. The coupling reaction may be enhanced by the addition of 1-hydroxybenzotriazole or similar additives. Reaction of the amide (12) with Lawesson's reagent in the presence of a base such as pyridine at a temperature preferably between 80–120° C. yields the appropriately-substituted 5-aminothiazoles (X).

An appropriately-substituted isothiocyanate (2) is reacted with an aminoalcohol in a suitable solvent such as dioxane to yield the thiourea. Treatment of the thiourea with 2-chloro-3-ethylbenzoxazolium tetrafluoroborate in the presence of a base such as TEA in a solvent such as acetonitrile yields desired 2-amino-1,3-oxazolines (XII). Aminoalcohols (14) are either commercially available or can be readily prepared by several methods. One method is reduction of azidoketones of the type described in schemes 15a–15d, either by catalytic hydrogenation in the presence of Pd/C in a solvent such as EtOH or EtOAc, or by a hydride reagent such as lithium aluminum hydride in a solvent such as dioxane or THF.

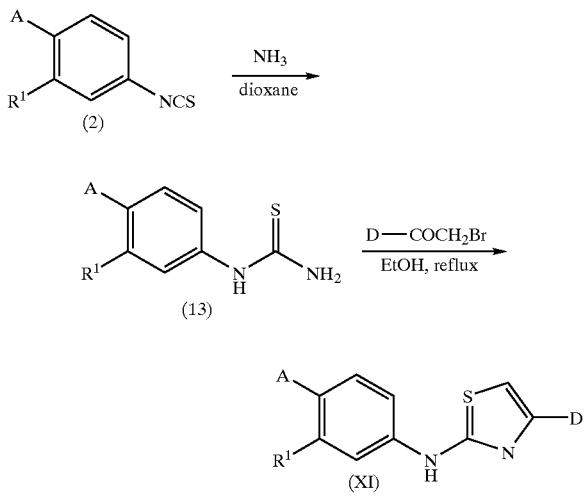

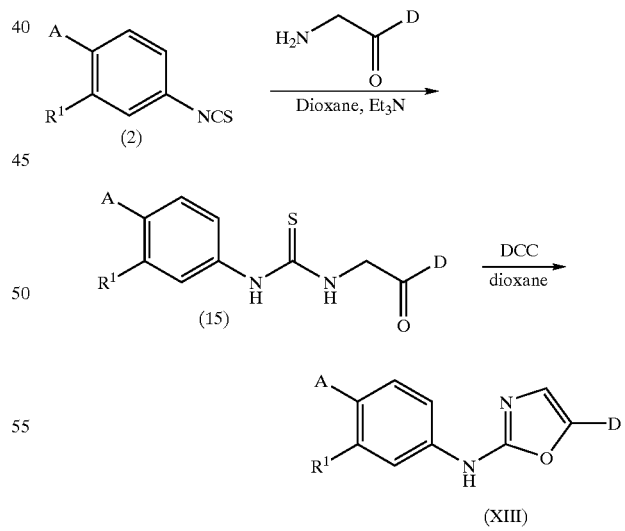

Reaction of an isothiocyanate (2) with ammonia in a solvent such as dioxane yields thiourea (12). Treatment of the thiourea (13) with an acylbromide, in the presence of a solvent such as EtOH or dioxane, at a temperature preferably between 60° C. and 110° C., yields the desired 2-amino-1,3-thiazoles (XI). Acyl bromides are either commercially available or readily prepared by methods known in the field.

Reaction of an isothiocyanate (2) with a β-ketoamine in the presence of a base such as TEA and a solvent such as dioxane yields the thiourea (15). Reaction of the thiourea in the presence of a dehydrating agent such as dicyclohexyl-carbodiimide or EDC, in a solvent such as dioxane or toluene, at a temperature preferably between 60° C. and 110° C., yields the desired 2-aminooxazoles (XIII). β-ketoamines are either commercially available or can be readily prepared by several methods. One method is reduction of azidoketones of the type described in schemes 15a–15d, by phosphine reagents such as triphenylphosphine in a solvent such as dioxane, followed by the addition of water or dilute ammonium hydroxide.

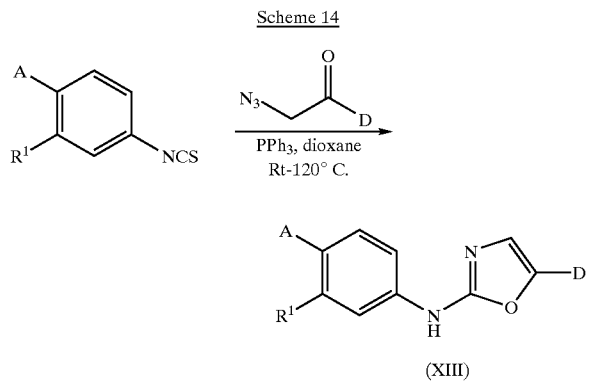

(XIII)

Reaction of an appropriately-substituted isothiocyanate (2) with an acylazide of the type described in schemes 15a–15d in the presence of a phosphine such as triphenyphosphine in a solvent such as DCM or dioxane at a temperature from rt to 100° C., also yields compounds (XIII). One skilled in the field will recognize that caution should be exercised while handling organic azides.

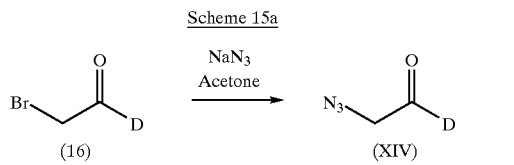

Treatment of the α-bromoketone (16) with sodium azide in a solvent such as acetone, generally at rt, yields the desired α-azidoketones (XIV) useful as intermediates in this invention. α-Bromoketones (16) are commercially available. Alternatively, α-bromoketones can be readily prepared from a ketone [CH$_3$—C(=O)D], by (a) reaction with a brominating agent such as bromine in acetic acid or pyridinium bromide perbromide and 30% hydrobromic acid; (b) reaction with a carboxylic acid, iso-butylchloroformate and N-methylmorpholine to provide the mixed anhydride, which on treatment with diazomethane (CH$_2$N$_2$) gives the α-diazoketone. Reaction of the α-diazoketone with either HBr gas in a solvent such as ether or dioxane, or aqueous 48% HBr, provides the α-bromoketone (16); or (c) reaction with sulfuric acid and bromine which yields the α,α-dibromoketone, which on treatment with diethylphosphite and TEA yields the α-(mono)bromoketone (16).

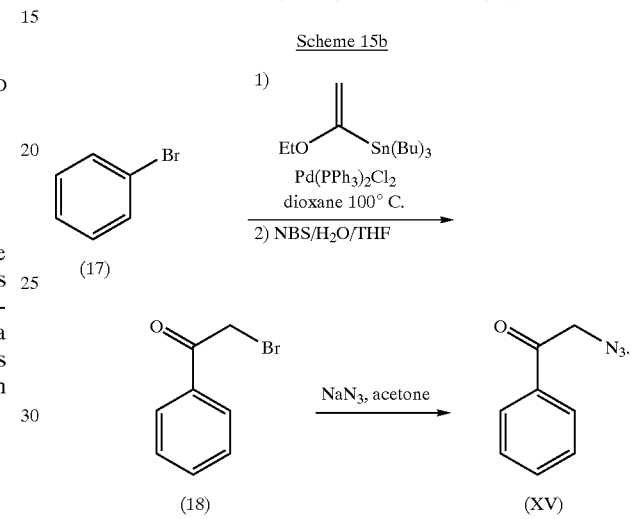

Reaction of an aryl bromide (17) with tributyl(1-ethoxyvinyl) tin and bis-(triphenylphosphine)palladium dichloride provides an intermediate enol ether. Treatment of the enol ether with N-bromosuccinamide at a temperature from 0° C. to rt yields the α-bromoketone (18). As described in 15a, treatment of the α-bromoketone with sodium azide in acetone gives the α-azidoketone (XV).

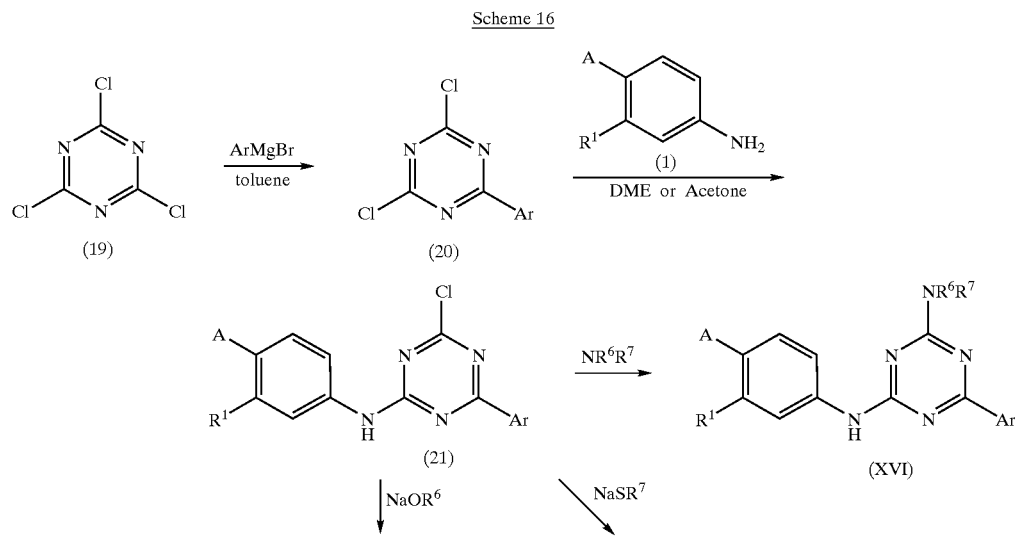

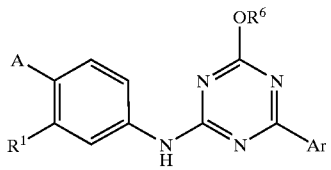

(XVI)

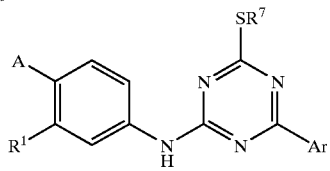

(XVI)

Reacting a commercially available cyanuric halide (19) such as cyanuric chloride with an aryl Grignard reagent yields the 2-aryl substituted-4,6-dichlorotriazine (20). Treatment of the dichlorotriazine (20) with an aniline (1) in a solvent such as acetone or dioxane with or without the addition of a base such as potassium carbonate, yields the intermediate 2-arylamino-6-aryl-4-chloro triazine (21). The remaining chloro group on the triazine may be replaced with an amine ($NR_6R_7$), in a solvent such as dioxane at a temperature preferably between 60–140° C.; with a sodium salt of a thiol ($NaSR_7$) in an inert solvent; or with a sodium alkoxide ($NaOR_6$) in an appropriate alcoholic or inert solvent such as dioxane or toluene to provide triazines of type (XVI).

Scheme 17

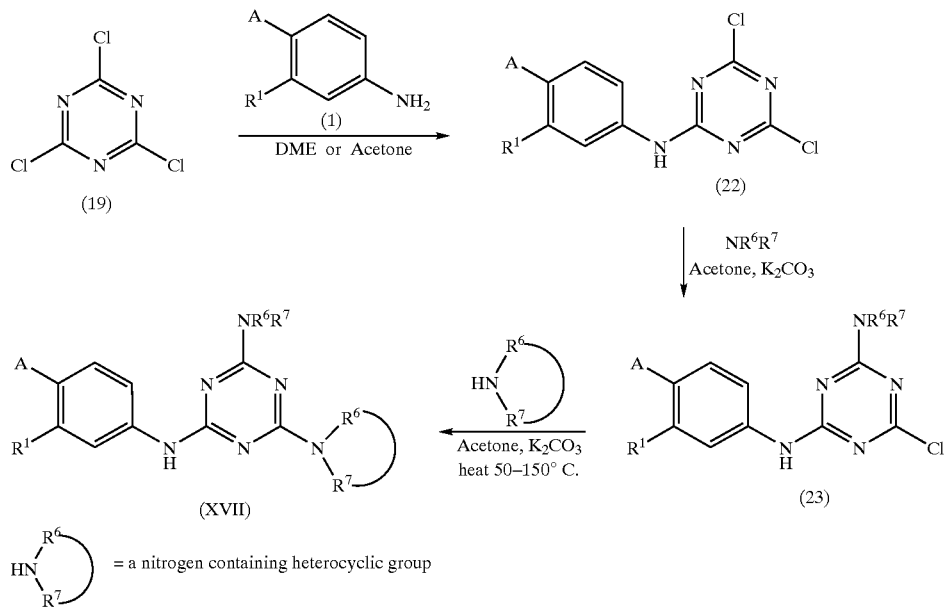

Consecutive displacement of the chloro groups in cyanuric chloride by nucleophiles can be accomplished by careful choice of reaction conditions with particular attention to the reaction temperature and order of nucleophile addition. (See, e.g., monosubstitution of cyanuric cloride in Cambell et a.., J. Org. Chem., 26, 2786 (1961); disubstitution of a triazine in Thurston et al., J. Amer. Chem. Soc. 73, 2981 (1954); and trisubstitution shown in Controulis et al, J. Amer. Chem. Soc. 67, 1946, (1945)). In the above Scheme 17, reaction of cyanuric chloride (19) with an aniline (1) at a temperature preferably between −45° C. and rt yields the 2-arylamino-4,6-dichlorotriazine (22). Addition of a second amine to the 2-arylamino-4,6-dichlorotriazine (22) at an extended period of time at rt (or preferably less than 40° C.), provides the monochlortriazine intermediate (23). Treatment of the intermediate (23) with an amine at a temperature preferably between 60° C. and 140° C. provides the trisubstituted triazine (XVII).

Scheme 18

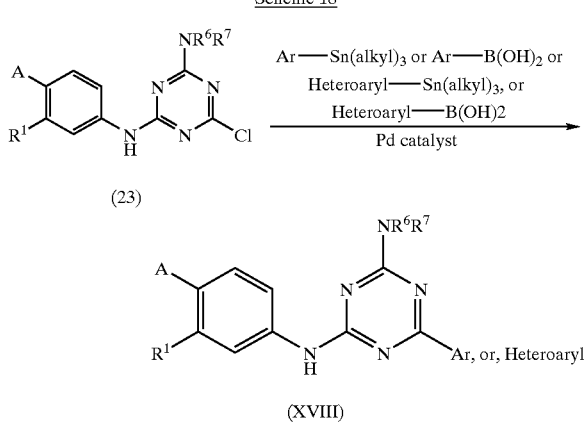

Monochlorotriazine intermediate (23) (see Scheme 17), is coupled with an aryl(trialkyl)tin or arylboronic acid or heteroaryl(trialkyl)tin or heteroarylboronic acid, in the presence of a palladium catalyst such as $Pd(PPh_3)_4$ to provide aryl or heteroaryl substituted triazines of type (XVIII).

Scheme 19

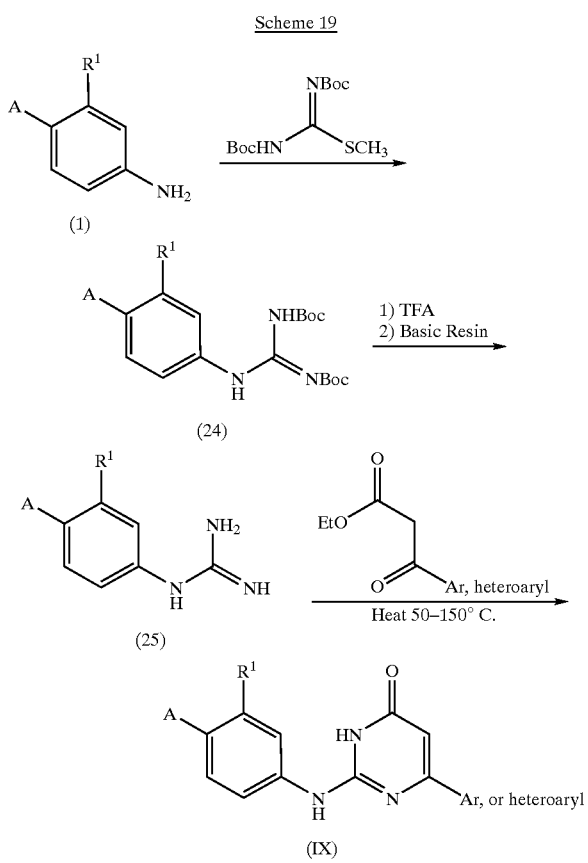

Reaction of an appropriately-substituted aniline (1) with 1,3 bis(tert-butoxycarbonyl)-2-methyl-2-thiopseudourea and TEA yields the bis-tert-butoxycarbonylguanidine (24). Cleavage of Boc groups using an acid such as TFA or 4N HCl in dioxane yields the guanidine salt (25). There are many methods of liberating the free base of a guanidine including treatment with a base, such as sodium methoxide in anhydrous MeOH, followed by filtration to remove the salt, or stirring with a commercially available strongly basic resin, followed by filtration, and evaporation of the solvent. The guanidine was treated with a β-ketoester and heated in a suitable solvent such as EtOH or dioxane at a temperature preferably between 50°C.–150° C. to yield the pyrimidinone (XI). More than one isomeric pyrimidone may be produced during this reaction, and the desired product may require purification by chromatography or recrystalization. Pyrimidones are also useful intermediates and can be readily converted to the chloropyrimidine by treatment with phosphoryl chloride. Displacement of the chloro group of pyrimidines can be accomplished with a variety of nucleophiles in a manner similar to that described in Scheme 16.

Scheme 20

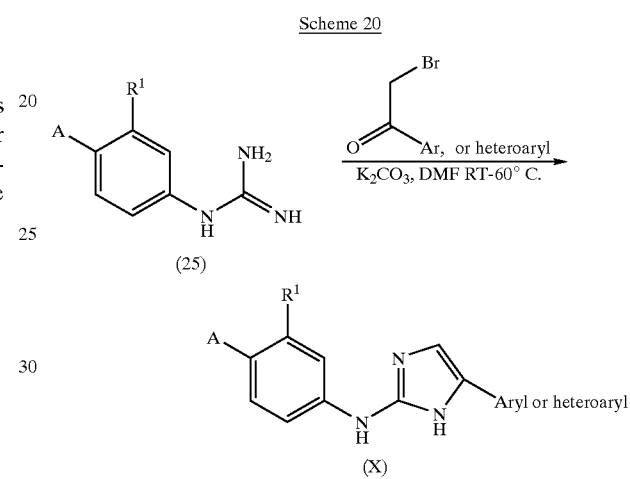

Reaction of guanidine (25) (see Scheme 19) with an α-bromoketone in the presence of a base such as potassium carbonate in a solvent such as DMF provides the desired 2-aminoimidazoles of type (X). More than one isomeric imidazole can form during this reaction, and the desired product can be obtained by a suitable chromatographic method or by recrystalization.

Scheme 21

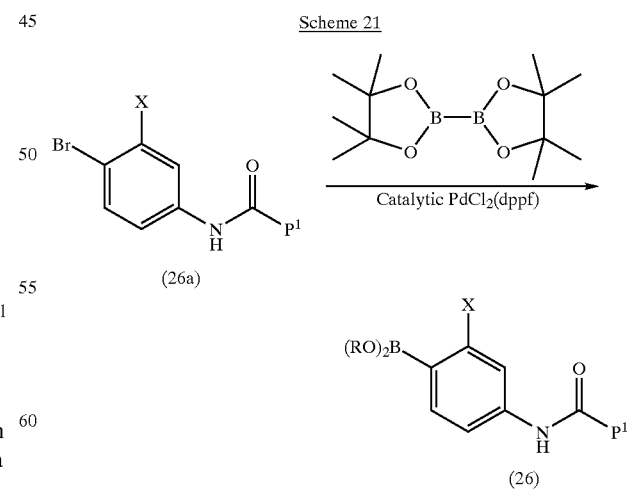

Aryl boronic acids and esters of type (26), where X is not Br or I, may be prepared from the corresponding arylbromide (26a) by treatment with a palladium catalyst such as

[1,1'-Bis(diphenylphosphino)-ferrocene] dichloropalladium (II) and bis(pinacolato)diboron, as reported by Ishayama et al., *J. Org. Chem.*, (1995) 7508–7510. Aryl boronic esters may be converted to the corresponding boronic acids by several methods including treatment with aqueous HCl. In a variation of the synthesis, the nitrogen may be masked as a nitro group and later reduced by several means including metal reductions, such as by treatment with tin chloride in HCl or by refluxing the nitro compound with zinc in the presence of $CaCl_2$ in a solvent such as EtOH, or in certain cases the nitro group may be reduced by catalytic hydrogenation in the presence of catalysts such as Pd/C. The conditions for the reduction of nitro groups are detailed in several references including Hudlicky, M., "Reductions in Organic Chemistry", 2nd Ed., ACS Monograph 188 (1996), pp. 91–101. In a second variation of the synthesis, the aryl bromide is allowed to remain through the entire synthesis and elaborated to the boronic acid at the end. This may eliminate the need for a protecting group.

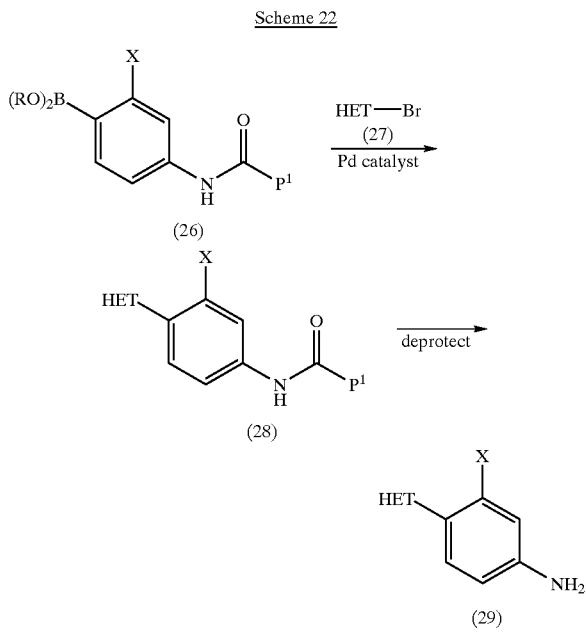

Suzuki-type cross coupling of an aryl boronic acid or ester (26) with an appropriate bromoheterocycle (27) in the presence of a suitable catalyst such as $Pd(PPh_3)_4$ yields the desired protected amide (28) (see, e.g., Miyaura et al., *Synth. Comm.*, 11(7) (1981), at pp. 513–19; Suzuki et. al., *J. Am. Chem. Soc.* 111:513 (1989); and Kalinin, *Russ. Chem. Rev.* 60:173 (1991)). The amide (28) may be deprotected as known to one skilled in the art (see, e.g., Greene and Wuts, *Protective Groups in Organic Synthesis,*" (John Wiley and Sons, Inc., New York, N.Y. 1991). For example, if the protecting group is acetyl, the product may be deprotected by treatment with aqueous KOH at a concentration of 0.5 N to 5 N at rt to 100° C. for a period between 0.5 h and 24 h, to provide amine (29), an intermediate for making compounds according to the invention. Compounds (26) can be prepared as shown in scheme 21.

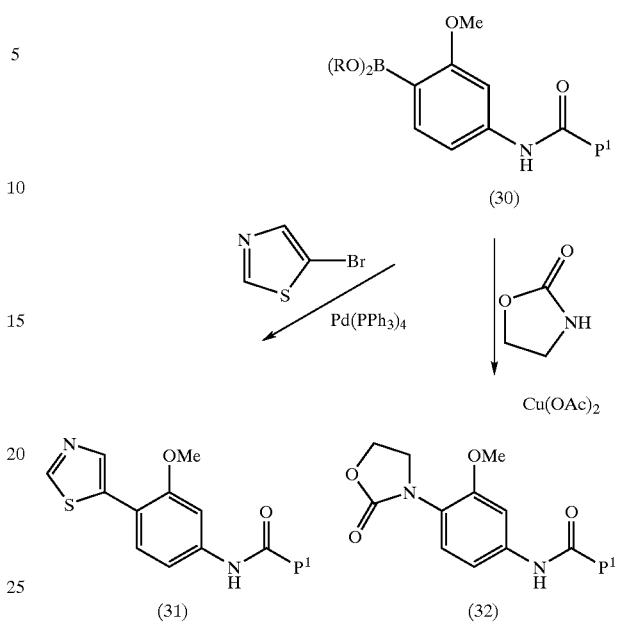

Aryl boronic acid (30) may be reacted with 5-bromothiazole in the presence of $Pd(PPh_3)_4$, to provide (31). Alternatively, aryl boronic acid (30) may be reacted with oxazolone in the presence of copper (II) acetate and an amine base such as pyridine to provide intermediate (32). Compounds (31) and (32) may be deprotected by an appropriate method. Copper has been shown to be an effective catalyst for cross coupling of aryl boronic acids to N-unsubstituted heterocycles as described by Chan. et al., *Tetrahed. Lett.* 39:2933–2936 (1998); and Lam et al., *Tetrahed. Lett.* 39:2941–2944 (1998). This results in compounds in which the heterocycle is attached to the aryl ring through nitrogen rather than carbon.

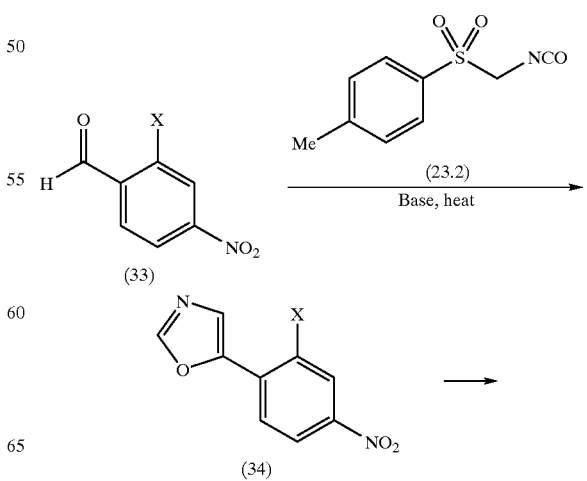

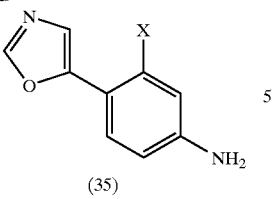

(35)

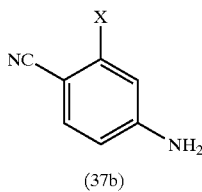

(37b)

Oxazoles may be prepared by 1,3 dipolar cycloaddition of the corresponding aldehyde (33) and (p-tolylsulfonyl) methyl isocyanate (TOSMIC) (34). The aldehyde may be commercially available or prepared from the corresponding methyl group by oxidation with reagents such as $CrO_3$, $MnO_2$, and ammonium cerium (IV) nitrate. These methods are well known to one skilled in the art and described in Hudlicky, M., "Oxidations in Organic Chemistry", ACS Monograph 186 (1990). The nitro group in intermediate (34) is reduced to an amine (35) as discussed above in Scheme 23. Synthesis of 5-membered heterocycles by 1,3-dipolar cycloaddition is also described by Padwa, "1,3-Dipolar Cycloaddition Chemistry," Vols. 1 & 2 (John Wiley and Sons, New York, N.Y., 1984).

Halonitrobenzenes (36) are either commercially available or can be readily prepared by methods known to one skilled in the art. Displacement of halonitrobenzenes (36) with a variety of nucleophiles produces compounds of structure (37). In one example, heating (36a) with a nucleophilic heterocycle such as triazole with or without the addition of a base provides the intermediate nitro compound which may be reduced as previously described to provide amines (37a). Alternatively, simple organic nucleophiles such as cyanide can be reacted with halonitrobenzene (36b) to provide an intermediate nitrocompound which can be reduced by many methods to produce amine (37b).

Utility

The compounds of the present invention inhibit IMPDH enzyme and are thus useful in the treatment of disorders which are mediated by IMPDH. Additionally, inventive compounds are inhibitors of the activated coagulation serine protease known as Factor VIIa, and may inhibit other serine proteases such as Factor IXa, Factor Xa, Factor XIa, thrombin, trypsin, tryptase, and/or urokinase. Thus, the compounds are useful for treating or preventing those processes which involve the production or action of Factor VIIa and/or other serine proteases.

The compounds of the present invention may be used to treat a variety of diseases including, but not limited to, transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, in the treatment of autoimmune diseases, such as rheumatoid arthritis, psoriatic arthritis, multiple sclerosis, juvenile diabetes, asthma, inflammatory bowel disease (such as Crohn's disease and ulcerative colitus), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Grave's disease, Hashimoto's thyroiditis, autoimmune thyroiditis, Behcet's or Sjorgen's syndrome (dry eyes/mouth), pernicious or immunohaemolytic anaemia, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, viteligo (depigmentation of the skin), alopecia areata, autoimmune alopecia, autoimmune hypopituatarism, Guillain-Barre syndrome, and alveolitis; in the treatment of T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); in the treatment of inflammatory diseases such as osteoarthritis, acute pancreatitis, chronic pancreatitis, asthma, acute respiratory distress syndrome, Sezary's syndrome and vascular diseases which have an inflammatory and or a proliferative component such Scheme 25

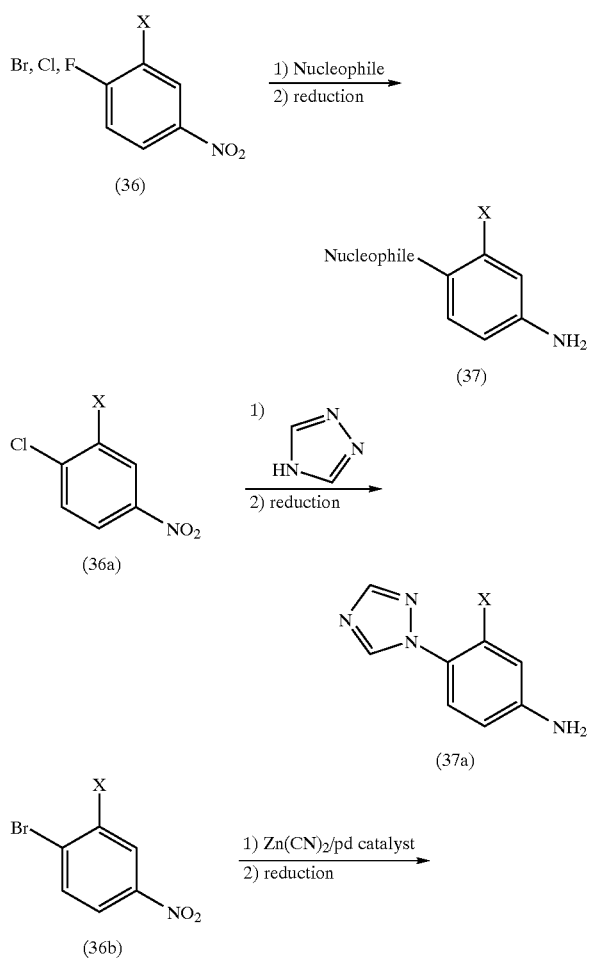

as restenosis, stenosis and artherosclerosis; in the treatment of cancer and tumor disorders, such as solid tumors, lymphomas and leukemia; in the treatment of fungal infections such as mycosis fungoides; in protection from ischemic or reperfusion injury such as ischemic or reperfusion injury that may have been incurred during organ transplantation, myocardial infarction, stroke or other causes; in the treatment of DNA or RNA viral replication diseases, such herpes simplex type 1 (HSV-1), herpes simplex type 2 (HSV-2), hepatitis (including hepatitis B and hepatitis C) cytomegalovirus, Epstein-Barr, and human immunodeficiency virus (HIV).

Additionally, IMPDH is also known to be present in bacteria and thus may regulate bacterial growth. As such, the IMPDH-inhibitor compounds of the present invention may be useful in treatment or prevention of bacterial infection, alone or in combination with other antibiotic agents.

In view of their above-referenced serine protease inhibitory activity, the inventive compounds are useful in treating consequences of atherosclerotic plaque rupture including cardiovascular diseases associated with the activation of the coagulation cascade in thrombotic or thrombophilic states. Such diseases include arterial thrombosis, coronary artery disease, acute coronary syndromes, myocardial infarction, unstable angina, ischemia resulting from vascular occlusion cerebral infarction, stroke and related cerebral vascular diseases (including cerebrovascular accident and transient ischemic attack). Additionally, the compounds are useful in treating or preventing formation of atherosclerotic plaques, transplant atherosclerosis, peripheral arterial disease and intermittent claudication. In addition, the compounds can be used to prevent restenosis following arterial injury induced endogenously (by rupture of an atherosclerotic plaque), or exogenously (by invasive cardiological procedures such as vessel wall injury resulting from angioplasty).

In addition, the inventive compounds are useful in preventing venous thrombosis, coagulation syndromes, deep vein thrombosis (DVT), disseminated intravascular coagulopathy, Kasabach-Merritt syndrome, pulmonary embolism, cerebral thrombosis, atrial fibrillation, and cerebral embolism. The compounds are useful in treating peripheral arterial occlusion, thromboembolic complications of surgery (such as hip replacement, endarterectomy, introduction of artificial heart valves, vascular grafts, and mechanical organs), implantation or transplantation of organ, tissue or cells, and thromboembolic complications of medications (such as oral contraceptives, hormone replacement, and heparin, e.g., for treating heparin-induced thrombocytopenia). The inventive compounds are useful in preventing thrombosis associated with artificial heart valves, stents, and ventricular enlargement including dilated cardiac myopathy and heart failure. The compounds are also useful in treating thrombosis due to confinement (i.e. immobilization, hospitalization, bed rest etc.).

These compounds are also useful in preventing thrombosis and complications in patients genetically predisposed to arterial thrombosis or venous thrombosis (including activated protein C resistance, $FV_{leiden}$, Prothrombin 20210, elevated coagulation factors FVII, FVIII, FIX, FX, FXI, prothrombin, TAFI and fibrinogen), elevated levels of homocystine, and deficient levels of antithrombin, protein C, and protein S. The inventive compounds may be used for treating heparin-intolerant patients, including those with congenital and acquired antithrombin III deficiencies, heparin-induced thrombocytopenia, and those with high levels of polymorphonuclear granulocyte elastase.

The present compounds may also be used to inhibit blood coagulation in connection with the preparation, storage, fractionation, or use of whole blood. For example, the compounds may be used to maintain whole and fractionated blood in the fluid phase such as required for analytical and biological testing, e.g., for ex vivo platelet and other cell function studies, bioanalytical procedures, and quantitation of blood-containing components. The compounds may be used as anticoagulants in extracorpeal blood circuits, such as those necessary in dialysis and surgery (such as coronary artery bypass surgery); for maintaining blood vessel patency in patients undergoing transluminal coronary angioplasty, vascular surgery including bypass grafting, arterial reconstruction, atherectomy, vascular graft and stent patency, tumor cell metastasis, and organ, tissue, or cell implantation and transplantation.

In a particular embodiment, compounds of the present invention are useful for treating any one or more of the aforementioned disorders irrespective of their etiology, e.g., for treating arterial thrombosis, coronary artery disease, acute coronary syndromes, myocardial infarction, unstable angina, ischemia, transplant rejection, rheumatoid arthritis, inflammatory bowel disease, and/or viral infections.

The present invention also provides pharmaceutical compositions comprising at least one compound of formula I, or a salt thereof, capable of treating an IMPDH-associated disorder and/or a Factor-VIIa associated disorder, in an amount effective therefor, alone or in combination with at least one additional therapeutic agent, and any pharmaceutically acceptable carrier, adjuvant or vehicle. "Additional therapeutic agent" encompasses, but is not limited to, an agent or agents selected from the group consisting of an immunosuppressant, anti-cancer agent, anti-viral agent, anti-inflammatory agent, anti-fungal agent, antibiotic, anti-vascular hyperproliferation compound, potassium channel opener, calcium channel blocker, sodium hydrogen exchanger inhibitor, anti-arrhythmic agent, thrombin inhibitor, platelet aggregation inhibitor or anti-platelet agent, fibrinogen antagonist, diuretic, anti-hypertensive agent, mineralocorticoid receptor antagonist; phospodiesterase inhibitor; cholesterol/lipid lowering agent; anti-diabetic agent; angiogenesis modulator; anti-coagulant; anti-proliferative agent; anti-tumor agent; and/or anti-infective agent. In the methods of the present invention, such other therapeutic agent(s) may be administered prior to, simultaneously with or following the administration of the compound(s) of the present invention.

Examples of suitable other anti-inflammatory agents with which the inventive compounds may be used include aspirin, non-steroidal antiinflammatory drugs (NSAIDs) (such as ibuprofen and naproxin), TNF-α inhibitors (such as tenidap and rapamycin or derivatives thereof), or TNF-α antagonists (e.g., infliximab, OR1384), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists, CD40 ligand antagonists, other IMPDH inhibitors, such as mycophenolate (CellCept®), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac® and Maxi-K® openers such as those disclosed in U.S. Pat. No. 6,184,231 B1), or other NF-κB inhibitors, such as corticosteroids, calphostin, CSAIDs, 4-substituted imidazo [1,2-A]quinoxalines as disclosed in U.S. Pat. No. 4,200,750; Interleukin-10, glucocorticoids, salicylates, nitric oxide, and other immunosuppressants; and nuclear translocation inhibitors, such as deoxyspergualin (DSG).

Examples of suitable other antibiotics with which the inventive compounds may be used include cyclosporins (e.g., cyclosporin A), CTLA4-Ig, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins constructed from CD40 and/or CD154/gp39 (e.g., CD40Ig and CD8gp39), β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable other antifungal agents with which the inventive compounds may be used include fungal cell wall inhibitors (e.g., candidas), azoles (e.g., fluoconazole and vericonazole), and membrane disruptors (e.g., amphotericin B). Examples of suitable other antiviral agents for use with the inventive compounds include nucleoside-based inhibitors, protease-based inhibitors, viral-assembly inhibitors, and other antiviral agents such as abacavir.

Additionally, the inventive compounds may be used in combination with aspirin, clopidogrel, ticlopidine or CS-747, warfarin, and low molecular weight heparins (such as lovenox, enoxaparain, and dalteparin). Other suitable therapeutic agents in combination with which the inventive compounds may be used include anti-arrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel openers such as $I_{Ach}$ inhibitors, and $I_{Kur}$ inhibitors (e.g., compounds such as those disclosed in U.S. application Ser. No. 09/729,731, filed Dec. 5, 2000; alpha- or beta-adrenergic blockers (such as propranolol, nadolol and carvedilol), or -β-adrenergic agonists such as albuterol, terbutaline, formoterol, salmeterol, bitolterol, pilbuterol, and/or fenoterol; angiotensin-II receptor antagonists (e.g., irbesartan, losartan or valsartan); anticholinergics such as ipratropium bromide; anti-diabetic agents such as biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), and dipeptidyl peptidase IV (DP4) inhibitors; anti-bodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CCD154 (a.k.a. "gp39"), such as antibodies specific for CD40 and/or CD154, fusion proteins constructed from CD40 and/or CD154/gp39 (e.g., CD40 Ig and CD8gp39); anti-hypertensive agents such as angiotensin-converting enzyme (ACE) inhibitors (e.g., captopril, lisinopril, zofenopril, ramipril, fosinopril, enalapril, ceranopril, cilazopril, delapril, pentopril, quinapril), vasopeptidase inhibitors, i.e., dual ACE/NEP inhibitors (e.g., omapatrilat and gemopatrilat), AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; angiogenesis modulators such as endostatin; anti-oxidant agents and/or lipid peroxidation inhibitors such as probucol, BO-653, Vitamin A, Vitamin E, AGI-1067; anti-platelet agents such as GPIIb/GPIIIa blockers, (e.g., abciximab, eptifibatide, tirofiban); $P2Y_{12}$ antagonists (e.g., clopidogrel, ticlopidine, CS-747); or thromboxane receptor antagonists (e.g., ifetroban); anti-proliferative agents such as methotrexate, leflunomide, FK506 (tacrolimus, Prograf), cytotoxic drugs such as azathiprine and cyclophosphamide, paclitaxel, and adriamycin; sodium hydrogen exchanger-1 (NHE-1) inhibitors such as cariporide; calcium channel blocking agents such as verapamil, nifedipine, diltiazem, amlodipine and mybefradil; cardiac glycosides such as digitalis and ouabain; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride; lipid profile modulators including HMG-CoA reductase inhibitors (e.g., pravastatin, simvastatin, atorvastatin, fluvastatin, cerivastatin, AZ4522, itavastatin [Nissan/Kowa]), ZD-4522 (a.k.a. rosuvastatin, or atavastatin or visastatin)); squalene synthetase inhibitors; fibrates; bile acid sequestrants (such as questran); ACAT1 inhibitors; ACAT2 inhibitors; dual ACAT1/2 inhibitors; MTP inhibitors; cholesterol absorption inhibitors; and cholesterol ester transfer protein inhibitors (e.g., CP-529414); PPAR-delta agonists; PPAR-alpha agonists; dual PPAR-alpha/delta agonists; LXR-alpha agonists; LXR-beta agonists; LXR dual alpha/beta agonists; mineralocorticoid receptor antagonists such as spironolactone and eplirinone. thrombolytic agents, such as tissue plasminogen activator (natural or recombinant), streptokinase, reteplase, activase, lanoteplase, urokinase, prourokinase, tenecteplase (TNK), lanoteplase (nPA), anisolated streptokinase plasminogen activator complex (ASPAC), Factor VIIa inhibitors, Factor Xa inhibitors, thrombin inhibitors (such as hirudin and argatroban), animal salivary gland plasminogen activators, PAI-1 inhibitors such as XR-330 and T-686, and inhibitors of α-2-antiplasmin such as anti-α-2-antiplasmin antibody, prostacyclin mimetics.

The above other therapeutic agents, when employed in combination with the compounds of the present invention, may be used in the same dosage form with the compound of formula I, in different dosage forms, in those amounts indicated in the Physicians' Desk Reference (PDR), and/or as otherwise determined by one of ordinary skill in the art.

The compounds of the present invention may act in a synergistic fashion with one or more of the above agents to allow for increased efficacy and/or reduced doses of any of the above agents and therefore minimize potential hemorrhagic side-effects.

The term "pharmaceutically acceptable carrier, adjuvant or vehicle" refers to a carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl -β-cyclodextrins, or other solubilized derivatives may also be used to enhance delivery of the compounds of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to IMPDH-associated disorders.

IMPDH Assay

The compounds disclosed herein are capable of targeting and inhibiting IMPDH enzyme. Inhibition can be measured by various methods, including, for example, IMP dehydrogenase HPLC assays (measuring enzymatic production of XMP and NADH from IMP and NAD) and IMP dehydrogenase spectrophotometric assays (measuring enzymatic production of NADH from NAD). See, e.g., Montero et al., *Clinica Chimica Acta* 238:169–178 (1995). Additional assays known in the art can be used in ascertaining the degree of activity of a compound ("test compound") as an IMPDH inhibitor. The inventors used the following assay to determine the degree of activity of the compounds disclosed herein as IMPDH inhibitors:

Activity of IMPDH I and IMPDH II was measured following an adaptation of the method described in WO 97/40028. The reaction mixture was prepared containing 0.1M Tris pH 8.0, 0.1 M KCl, 3 mM EDTA, 2 mM DTT, 0.4 mM IMP and 40 nM enzyme (IMPDH I or IMPDH II). The reaction was started by the addition of NAD to a final concentration of 0.4 mM. The enzymatic reaction was followed by measuring the increase in absorbance at 340 nM that results from the formation of NADH. For the analysis of potential inhibitors of the enzyme, compounds were dissolved in DMSO to a final concentration of 10 mM and added to the assay mixture such that the final concentration of DMSO was 2.5%. The assay was carried out in a 96-well plate format, with a final reaction volume of 200 μl.

Factor VIIa Assay

Compound was prepared as a 5 mM stock in DMSO, diluted further in DMSO and added directly to the assays. The DMSO concentration for all Factor VIIa studies was less than 1% and compared to DMSO vehicle controls.

Human Factor VIIa was obtained from Enzyme Research Labs (Cat.# HFVIIA 1640). Human recombinant tissue factor (INNOVIN from Dade Behring Cat.# B4212-100; "20 ml vial") was diluted with 8 ml of $H_2O$ per vial and diluted further 1:30 into the 302 μl final assay volume. Tissue factor activated FVIIa enzymatic activity was measured in a buffer containing 150 mM NaCl, 5mM $CaCl_2$, 1 mM CHAPS and 1 mg/ml PEG 6000 (pH 7.4) with 1 nM FVIIa and 100 μM D-Ile-Pro-Arg-AFC (Enzyme Systems Products, Km>200 μM) 0.66% DMSO. The assay (302 μl total volume) was incubated at RT for 2 hr prior to reading fluorometric signal (Ex 405/Em 535) using a Victor 2 (Wallac) fluorescent plate reader.

Compounds disclosed herein are capable of inhibiting the enzyme IMPDH and/or Factor VIIa at a measurable level under the above-described assays or other assays known in the field.

The following examples illustrate preferred embodiments of the present invention and do not limit the scope of the present invention which is defined in the claims. Abbreviations employed in the Examples and Schemes previously set forth are defined below.

| Abbreviations | |
|---|---|
| Ac | Acetyl |
| AcOH | Acetic acid |
| aq. | Aqueous |
| CDI | Carbonyldiimidazole |
| Bn | Benzyl |
| Boc | tert-butoxycarbonyl |
| DCM | Dicholormethane |
| DMAP | Dimethylaminopyridine |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| h | Hours |
| i | iso |

| Abbreviations -continued | |
|---|---|
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| $M^+$ | $(M+H)^+$ |
| $M^{+1}$ | $(M+H)^+$ |
| MS | Mass spectrometry |
| n | normal |
| Pd/C | Palladium on carbon |
| Ph | Phenyl |
| Pr | Propyl |
| Ret Time | Retention time |
| RP | Reserve phase |
| rt or RT | room temperature |
| sat. | Saturated |
| $Pd(PPh_3)_4$ | tetrakis (triphenylphosphine) palladium |
| TEA | triethylamine |
| THF | Tetrahydrofuran |
| TFA | Trifluoroacetic acid |
| TOSMIC | Tosylmethyl isocyanide |
| YMC | YMC Inc, Wilmington, NC 28403 |

EXAMPLE 1

$N^3$-[3-Methoxy-4-(5-oxazolyl)phenyl]-1-(2-pyridinyl)-1H-1,2,4-triazole-3,5-diamine

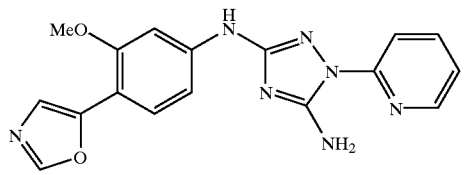

Example 1 Part A. N-Cyano-N'-(3-methoxy-4-(5-oxazolyl)phenyl)-O-phenylisourea

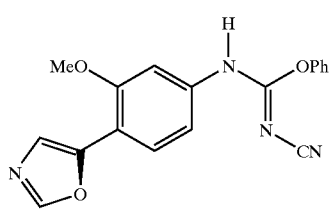

1A

A mixture of 5-(4-amino-2-methoxyphenyl)oxazole (0.200 g, 1.05 mmol) and diphenyl cyanocarbonimidate (0.258 g, 1.05 mmol) in 10 mL of acetonitrile was stirred at reflux for 40 h. As the reaction mixture cooled to rt, a yellow solid precipitated out of solution. The volume of solvent was reduced by half, and ether was added. Vacuum filtration afforded 1A (0.330 g, 94%) as a pale yellow solid which was 97% pure by LC/MS (retention time=3.48 min.; $M^+$=335.15. Column: YMC S5 ODS 4.6×5.0 mm Ballistic. Solvent A=10% MeOH, 90% $H_2O$, 0.1% TFA; Solvent B=90% MeOH, 10% $H_2O$, 0.1% TFA).

Example 1 Part B. $N^3$-[3-Methoxy-4-(5-oxazolyl) phenyl]-1-(2-pyridinyl)-1H-1,2,4-triazole-3,5-diamine A solution of 1A (150.0 mg, 0.422 mmol) and 2-hydrazinopyridine (92.0 mg, 0.843 mmol) in acetonitrile (5.0 mL) was heated at reflux for 16 h. After cooling to RT, the solution was diluted with AcOEt, washed with water and brine, and dried over anhydrous MgSO$_4$. The solvent was removed under vacuum, and the residue was washed first with diethyl ether and then with MeOH to give Example 1 (15.0 mg, 10%) as a beige solid. The product was 99% pure by LC/MS (retention time=3.60 min.; M$^+$=350.10. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 2

1-Cyclohexyl-N$^5$-[3-methoxy-4-(5-oxazolyl) phenyl]-1H-1,2,4-triazole-3,5-diamine and 1-Cyclohexyl-N$^3$-[3-methoxy-4-(5-oxazolyl)phenyl]-1H-1,2,4-triazole-3,5-diamine

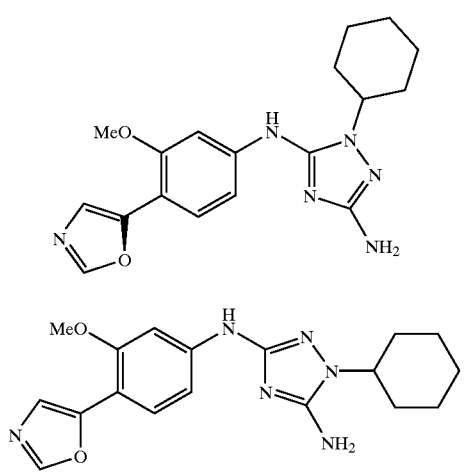

Example 2 Part A. 4-Nitro-2-methoxy-(α,α bisacetoxy)toluene

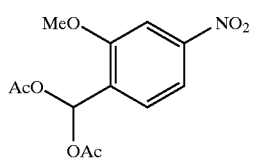

2A

A mixture of 4-nitro-2-methoxytoluene (150.0 g, 0.8973 mol), HOAc (900 mL) and Ac$_2$O (900 mL) was stirred and cooled to 8° C. with an acetone/ice bath. Concentrated H$_2$SO$_4$ (136 mL) was carefully added while keeping the reaction temperature below 19° C. After cooling to 0° C., CrO$_3$ (252.6 g, 2.526 mol, 2.815 equiv.) was added portion-wise over 1 hour while maintaining the reaction temperature between 0–10° C. After the addition, the mixture was stirred at 0° C. for 30 minutes at which time the reaction was complete. The reaction mixture was then carefully poured into ice (1.5 kg) with stirring to give a slurry. The remaining black gummy residue was rinsed with HOAc (3×100 mL), and the washes were added to the slurry. After stirring for 10 minutes, the slurry was filtered. The cake was washed with water (3×400 mL) and suction dried for 17 hours to compound 2A (129.0 g, 51%). $^1$H NMR (CDCl$_3$) d 8.02 (s, 1H), 7.89 (d, J=8.4 Hz, 1H), 7.77 (s, 1H), (d 8.4 Hz, 1H), 3.98 (s, 3H), 2.16 (s, 6H).

Example 2 Part B. 4-Nitro-2-methoxybenzaldehyde

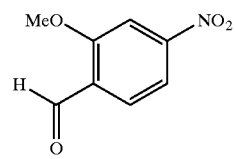

2B

A mixture of compound 2A (250.7 g, 0.8851 mol), dioxane (300 mL), and concentrated HCl (60 mL), was heated to reflux and stirred under N$_2$ for 20 hours. Water (250 mL) was added dropwise while maintaining the reaction mixture at reflux. After cooling to 0° C. with an ice/water bath, the resulting slurry was stirred for 30 minutes and then filtered. The cake was washed with water (4×200 mL) and suction dried for 17 hours to give 2B (146.3 g, 91%) as a yellow solid. $^1$H NMR (CDCl$_3$) d 10.54 (s, 1H), 8.00 (d, J=8.3 Hz, 1H), 7.91 (s, 1H), 7.89 (d, J=8.3 Hz, 1H), 4.08 (s, 3H).

Example 2 Part C. 5-(4-Nitro-2-methoxyphenyl) oxazole

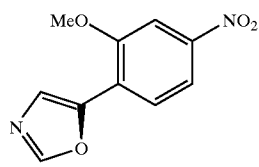

2C

A mixture of compound 2B (146.3 g, 0.8076 mol), TOSMIC (157.7 g, 0.8077 mol), K$_2$CO$_3$ (116.6 g, 0.8075 mol), and MeOH (2.5 L) was heated to reflux under N$_2$ and stirred for 3 hours. Water (1.25 L) was added drop-wise while maintaining the temperature between 59–69° C. The resulting slurry was cooled to room temperature, and then to 5° C. with an ice-water bath. After stirring for 30 minutes at 5° C., the slurry was filtered. The resulting cake was washed with water (3×400 mL) and dried in a vacuum oven at 45° C. for 20 hours to provide compound 2C (148.5 g, 84%) as a yellow-reddish solid. $^1$H NMR (CDCl$_3$) d 8.02 (s, 1H), 7.97 (d, J=2 Hz, 1H), 7.95 (d, J=2 Hz, 1H), 7.86 (s, 1H), 7.78 (s, 1H), 4.11 (s, 3H).

Example 2 Part D. 5-(4-Amino-2-methoxyphenyl) oxazole

2D

A mixture of compound 2C (130.0 g, 0.6131 mol), Pd/C (10%, 26.2 g), and absolute EtOH (1280 mL) was hydrogenated at 35–45psi H$_2$ until the reaction was complete. The mixture was filtered over a pad of celite (20 g) and the cake was washed with EtOH (3×100 mL). The filtrate was concentrated to a volume of 350 mL. Heptane (500 mL) was added to the resulting slurry. After stirring for 2 hours at rt, the slurry was filtered. The cake was washed with heptane (3×100 mL) and air-dried to give compound 2D (80.0 g). A second portion of product (30.2 g) was recovered from the mother liquor affording a total yield of 95%. $^1$H NMR (CDCl$_3$) d 7.88 (s, 1H), 7.60 (d, J=8.4 Hz, 1H), 7.41 (s, 1H), 6.41 (dd, J=8.4, 2.1 Hz, 1H), 3.34 (d, J=2.1 Hz, 1H), 3.98 (bs, 2H), 3.94 (s, 3H).

Example 2 Part E. 3-Methoxy-4-(5-oxazolyl)phenyl isothiocyanate

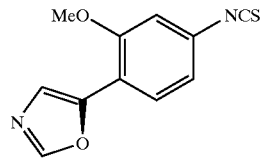

2E

A solution of 2D (3.50 g, 18.4 mmol) and 1,1'-thiocarbonyldi-2(2H)-pyridone (4.41 g, 18.4 mmol) in dichloromethane (100 mL) was stirred at RT for 3 h. The solvent was evaporated under vacuum, and the residue was subjected to column chromatography (30% AcOEt/hexane) to afford 2E (4.02 g, 94%) as white crystals.

Example 2 Part F. Sodium Cyanamide

To a solution of cyanamide (3.00 g, 71.4 mmol) in methanol (30 mL) was added sodium methoxide (0.5 M methanol solution, 143 mL, 71.4 mmol) at RT over 25 min, and the resulting solution was stirred at RT for 2 h. Evaporation of the solvent gave compound 2F (4.57 g, 100% yield) as a white solid.

Example 2 Part G. Sodium Salt of N-cyano-N'-(3-Methoxy-4-(5-oxazolyl)phenyl)thiourea

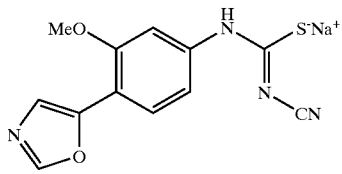

2G

To a solution of 2E (2.50 g, 10.8 mmol) in absolute EtOH (150 mL) was added 2F (sodium cyanamide; 691 mg, 10.8 mmol) in absolute EtOH (100 mL) at rt over 30 min. The resulting solution was stirred at RT for 4 h. Most of the solvent was evaporated under vacuum, and to the residue was added dichloromethane (60 mL). The precipitate was collected by filtration and washed with dichloromethane to provide 2G (2.15 g, 67%) as a white solid.

Example 2 Part H. Example 2' and 3"

To a solution of cyclohexylhydrazine hydrochloride (61.0 mg, 0.405 mmol) in DMF (5.0 mL) was added TEA (84.5 μL, 0.606 mmol), and the mixture was stirred at RT for 10 min. The precipitate produced was removed by suction filtration, and the filtrate was directly treated with compound 2G (60.0 mg, 0.202 mmol) and 1-ethyl-3-(3-dimethylaminopropyl)carbodiimide hydrochloride (74.4 mg, 0.404 mmol). The resulting mixture was heated at 60° C. for 16 h before it was diluted with AcOEt, washed with water, brine and dried over anhydrous MgSO$_4$. After the solvent was removed under vacuum, the residue was puri- fied by preparative HPLC, followed by neutralization with 10% Na$_2$CO$_3$, to afford Examples 2' (7.9 mg) and 2" (25.8 mg, 36%). Both products were white solids and 100% pure by LC/MS (for 2', retention time=3.30 min.; M$^+$=355.24. For 2", retention time=3.74 min.; M$^+$=355.24. Column: YMC S5 ODS 4.6×5.0 mm Ballistic. Solvent A=10% MeOH, 90% H$_2$O, 0.1% TFA; Solvent B=90% MeOH, 10% H$_2$O, 0.1% TFA).

EXAMPLE 3

6-[3-[[3-Methoxy-4-(5-oxazolyl)phenyl]amino]-1H-1,2,4-triazol-1-yl]-1,3-dimethyl-2,4(1H,3H)-pyrimidinetrione

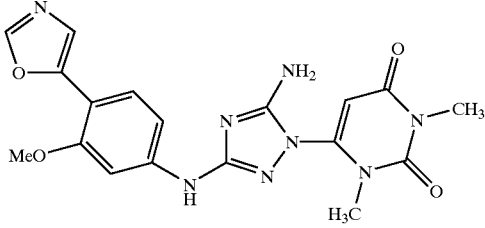

To a mixture of 2G (30.0 mg, 0.101 mmol) and 1-ethyl-3-(3-dimethylaminopropyl)carbodiimide hydrochloride (37.2 mg, 0.202 mmol) in DMF (3.0 mL) was added HN$_2$NH-D, wherein D is 1,3-dimethyl-2,4(1H,3H)-pyrimidinetrione. The resulting mixture was heated at 50° C. for 15 h, diluted with AcOEt, washed with water, brine, and dried over anhydrous MgSO$_4$. After the solvent was removed under vacuum, the residue was purified by preparative HPLC, to afford Example 3 in the form of a TFA salt. HPLC 3.280, MS (M+)=411.25.

EXAMPLE 4

N$^3$-[3-Methoxy-4-(5-oxazolyl)phenyl]-1-(3-pyridinyl)-1H-1,2,4-triazol-3,5-diamine

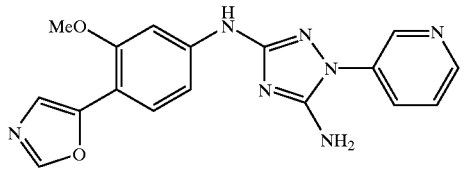

Example 4 Part A. 3-Pyridinohydrazine

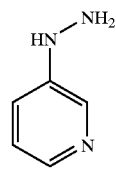

4A

To a solution of 3-aminopyridine (4.00 g, 42.5 mmol) in concentrated hydrochloric acid (25 mL) was added a solution of sodium nitrite (3.30 g, 46.4 mmol) in water (8 mL) at −5° C. over 10 min. The solution was stirred at 0° C. for 45 min and then to this solution was added a solution of Tin (II) chloride dihydrate in concentrated HCl (12 mL) at −5°

C. The resulting mixture was stirred at 0° C. for another hour. The solid that formed was collected by suction filtration and then placed in a beaker containing ice (20 g). To this mixture was added 50% KOH solution until it became basic (pH>10). The mixture was then extracted with AcOEt. The combined extract was dried over anhydrous MgSO$_4$. Evaporation of solvent under vacuum provided product 4A (1.34 g, 29% yield) as a yellow solid.

Example 4 Part B. N$^3$-[3-Methoxy-4-(5-oxazolyl) phenyl]-1-(3-pyridinyl)-1H-1,2,4-triazol-3,5-diamine A mixture of compound 2G (300.0 mg, 1.01 mmol), 1-ethyl-3-(3-dimethylaminopropyl)carbodiimide hydrochloride (387.0 mg, 2.02 mmol), and 3-pyridinehydrazine 4A (220.0 mg, 2.02 mmol) in DMF (10 mL) was subjected to the same procedure used in the preparation of Example 1 to afford the desired product (36.0 mg, 10% yield) as a yellow solid. (LC/MS; retention time=3.01 min.; M$^+$=350.17. Column: SHIMADZU 4.6×5.0 mm Ballistic. Solvent A=10% MeOH, 90% H$_2$O, 0.1% TFA; Solvent B=90% MeOH, 10% H$_2$O, 0.1% TFA.

EXAMPLE 5

N$^3$-[3-Methoxy-4-(-5-oxazolyl)phenyl]-1-(4-pyridinyl)-1H-1,2,4,-triazol-3,5-diamine

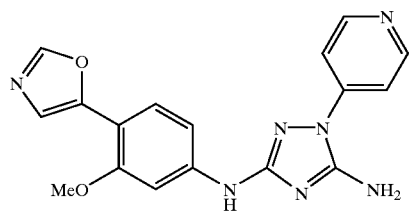

Example 5 Part A. 4-Pyridinohydrazine

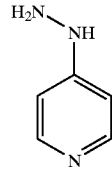

5A

A solution of 4-chloropyridine hydrochloride (500.0 mg, 3.33 mmol) and hydrazine monohydrate (1.67 g, 33.4 mmol) in ethanol (10 mL) was heated at 120° C. for 20 h. The solvent was evaporated under vacuum, and the residue was diluted with water (10 mL). To the resulting solution was added 50% NaOH solution until it became very basic. The solution was extracted with AcOEt. The combined extracts were dried over anhydrous MgSO$_4$. Evaporation of solvent gave the desired product (238.0 mg, 66% yield) as a reddish solid.

Example 5 Part B. N$^3$-[3-Methoxy-4-(-5-oxazolyl) phenyl]-1-(4-pyridinyl)-1H-1,2,4-triazol-3,5-diamine A mixture of compound 2G (272.0 mg, 0.918 mmol), 1-ethyl-3-(3-dimethylaminopropyl)carbodiimide hydrochloride (352.0 mg, 1.84 mmol), and 4-pyridinehydrazine 5A (200.0 mg, 1.84 mmol) in DMF (10 mL) was heated at 60° C. for 16 h. The mixture was then diluted with AcOEt (80 mL), washed with water and brine, and concentrated under vacuum. The residue was subjected to preparative HPLC, followed by neutralization with 10% Na$_2$CO$_3$ solution, to afford the desired product (27.4 mg, 8% yield) as a yellow solid. (LC/MS; retention time=2.83 min.; M$^+$=350.19. Column: SHIMADZU 4.6×5.0 mm Ballistic. Solvent A=10% MeOH, 90% H$_2$O, 0.1% TFA; Solvent B=90% MeOH, 10% H$_2$O, 0.1% TFA).

EXAMPLES 6–10

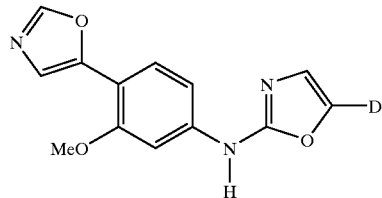

(Ic)

Compounds having formula (Ic), wherein D is as shown in Table I, were prepared by adding an appropriately-substituted azide to a solution of isothiocyanate 1E and phosphine, such as triphenylphosphine, in a solvent, such as DCM, 1,4-dioxane, 1,2-dimethoxyethane, THF, 1,2-dichloroethane or toluene. The solution was stirred at a temperature from rt to 120° C. for a period of 15 min to 24 h. The reaction generally proceeds in higher yield when conducted at a temperature between 65 and 110° C. which is conveniently maintained by the boiling point of the chosen solvent. When the reaction is conducted at a temperature between 65 and 110° C., the time for completion of the reaction is usually reduced to between 15 min and 1 h. Azides can be made by the methods outlined in Schemes 15a–b.

TABLE 1

| Example | D | Name | HPLC time (min) | M$^+$ |
|---|---|---|---|---|
| 6 | 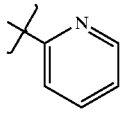 | N-[3-Methoxy-4-(5-oxazolyl)phenyl]-5-(2-pyridinyl)-2-oxazolamine | 3.3 | 335.20 |

TABLE 1-continued

| Example | D | Name | HPLC time (min) | M+ |
|---|---|---|---|---|
| 7 | | N-[3-Methoxy-4-(5-oxa-zolyl)phenyl]-5-(tetrahydro-2-furanyl)-2-oxazolamine | 3.39 | 328.21 |
| 8 | | 5-(2,3-Dihydro-1,4-benzo-dioxin-6-yl)-N-[3-methoxy-4-(5-oxazolyl)phenyl]-2-oxazolamine | 4.20 | 392.22 |
| 9 | | 5-(2-Furanyl)-N-[3-methoxy-4-(5-oxazolyl)phenyl]-2-oxazolamine | 4.05 | 324.18 |
| 10 | | 2-[2-[[3-Methoxy-4-(5-oxazolyl)phenyl]amino]-5-oxazolyl]-1-pyrrolidinecarboxylic acid phenylmethyl ester | 3.40 | 461.26 |

EXAMPLE 11

N-[3-Methoxy-4-(5-oxazolyl)phenyl]-5-(2-pyrrolidinyl)-2-oxazolamine

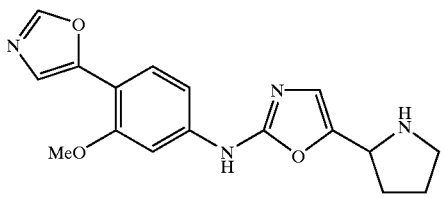

To a suspension of Pd/C (30 mg) in MeOH (2 ml) was added Example 10 (55 mg, 0.119 mmol) and ammonium formate (150 mg, 2.39 mmol). The mixture was stirred at RT for 3 hr and then diluted with AcOEt (60 ml). The solution was filtered and concentrated in vacuo to give the title compound as an oil (28 mg, 74%). (LC/MS retention time=2.60 min.; M+=327.22 Column: YMC S5 ODS 4.6× 5.0 mm Ballistic. Solvent A=10% MeOH, 90% H₂O, 0.1% TFA; Solvent B=90% MeOH, 10% H₂O, 0.1% TFA).

EXAMPLE 12

2-[2-[[3-Methoxy-4-(5-oxazolyl)phenyl]amino]-5-oxazolyl]-1-pyrrolidinecarboxylic acid methyl ester

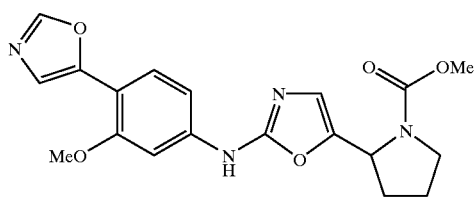

To a solution of 11 (86 mg 0.264 mmol) in THF (3 ml) and H₂O (3 ml) was added K₂CO₃ (47 mg, 0.342 mmol) followed by addition of methylchloroformate (265 μl, 0.343 mmol). The mixture was stirred at RT overnight and partitioned between AcOEt (50 ml) and H₂O (30 ml). The AcOEt layer was dried over Na₂SO₄ and concentrated in vacuo. The residue was triturated with ether to afford 11 (13 mg) as an off-white solid. (LC/MS retention time=3.46 min.; M+=385.22 Column: YMC S5 ODS 4.6×5.0 mm Ballistic. Solvent A=10% MeOH, 90% H₂O, 0.1% TFA; Solvent B=90% MeOH, 10% H₂O, 0.1% TFA).

EXAMPLES 12 to 16

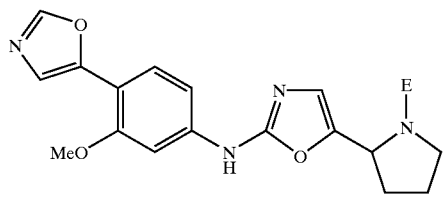
(Id)

Compounds having the formula (Id), wherein E has the values lited in Table 2, were prepared from Example 11 by a route analogous to that used in Example 12 but replacing methylchloroformate with the required reagents. The HPLC conditions for these examples were as follows: column: YMC S5 ODS 4.6×5.0 mm Ballistic. Solvent A=10% MeOH, 90% H2O, 0.1% TFA; Solvent B=90% MeOH, 10% H₂O, 0.1% TFA. Flow rate: 4 mL/min. Gradient: 4 min.

TABLE 2

| Example | E | Name | HPLC time (min) | M+ |
|---|---|---|---|---|
| 12 | (structure) | 2-[2-[[3-Methoxy-4-(5-oxazolyl)phenyl]amino]-5-oxazolyl]-N-methoxymethylcarbonyl pyrrolidine | 3.12 | 399.22 |
| 13 | (structure) | 2-[2-[[3-Methoxy-4-(5-oxazolyl)phenyl]amino]-5-oxazolyl]-N-[4-morpholinomethylcarbonyl]pyrrolidine | 2.86 | 454.36 |
| 14 | (structure) | 2-[2-[[3-Methoxy-4-(5-oxazolyl)phenyl]amino]-5-oxazolyl]-1-pyrrolidinecarboxylic acid ethyl ester | 3.01 | 399.22 |
| 15 | (structure) | 2-[2-[[3-Methoxy-4-(5-oxazolyl)phenyl]amino]-5-oxazolyl]-1-pyrrolidinecarboxylic acid 2-(methylsulfonyl)ethyl ester | 3.23 | 477.26 |
| 16 | (structure) | 2-[2-[[3-Methoxy-4-(5-oxazolyl)phenyl]amino]-5-oxazolyl]-1-pyrrolidinecarboxylic acid 3-tetrahydrofuranyl ester | 3.53 | 441.32 |

EXAMPLE 17

N-[3-Methoxy-4-(5-oxazolyl)phenyl]-N'-methyl-6-(1-pyrrolidinyl)-1,3,5-triazine-2,4-diamine

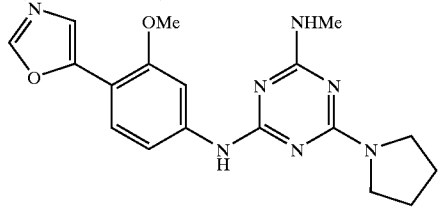

Cyanuric chloride (1.84 g, 10 mmol) and pulverized potassium carbonate (4.14 g, 30 mmol) were suspended in acetone (50 mL) and cooled in an ice salt bath. 4-Oxazol-5-yl-3-methoxyaniline (1.90 g, 10 mmol) was added dropwise and stirred for 2 h. The crude product was filtered and resuspended in 100 mL of 0.1N NaOH and 200 mL of EtOAc, and filtered. The product was dried to yield 2.12 g, 63% of the title compound. LCMS condition B retention time=3.47 min (100%) M+H+=338, 340 (100%, 70%).

Example 17 Part A. 2,4-Dichloro-6-(4-oxazol-5-yl-3-methoxyphenylamino)triazine

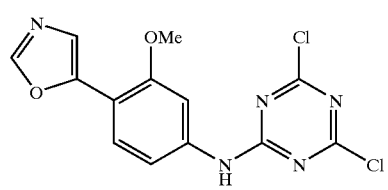
17A

Example 17 Part B. 2-Chloro-4-methylamino-6-(4-oxazol-5-yl-3-methoxyphenylamino)triazine

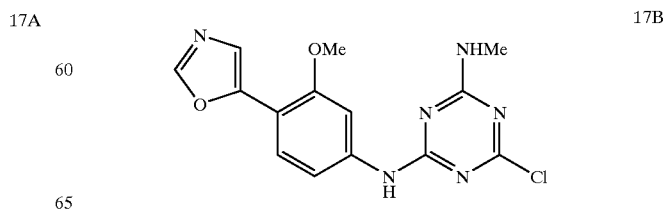
17B

Compound 17A (1.8 g, 5.4 mmol) was suspended in dimethoxyethane (50 mL). 2 M Methylamine in THF (27 mL, 54 mmol) was added dropwise and the reaction mixture stirred for 3 h. The crude product was filtered and triturated with ethanol (20 mL) and dried to yield 1.37 g (77%) of the title compound. LCMS Condition A retention time=2.61 min (>95%), M+H$^+$=333.16 (100%).

Example 17 Part C. N-[3-Methoxy-4-(5-oxazolyl) phenyl]-N'-methyl-6-(1-pyrrolidinyl)-1,3,5-triazine-2,4-diamine Compound 17B, (41 mg, 0.12 mmol) was suspended in dimethoxyethane (5 mL) and dimethylformamide (0.5 ml). Pyrrolidine (88 mg, 1.2 mmol) was added and the reaction mixture heated overnight at 50° C. The product was filtered and triturated with ether (5 mL) to yield 22.6 mg (50%) of the title compound. LCMS condition D retention time=3.47 min (100%) M+H$^+$=368.31 (100%).

EXAMPLES 18 to 44

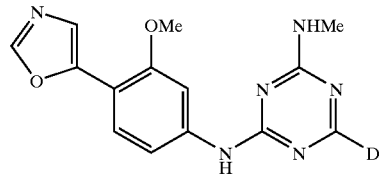

(Ie)

Compounds having the formula (Ie), wherein D has the values listed in Table 3 below were prepared in a manner similar to that described for N-[3-Methoxy-4-(5-oxazolyl) phenyl]-N'-methyl-6-(1-pyrrolidinyl)-1,3,5-triazine-2,4-diamine, (Example 17) from the intermediate 2-chloro-4-methylamino-6-(4-oxazol-5-yl-3-methoxyphenylamino) triazine (Example 17, Part B), or a similar intermediate usefull for this invention. The chlorotriazine intermediate was generally heated for 4–24 h in a solvent such as dimethoxyethane or THF in the presence of 5 to 10 equivalents of a desired amine. The product was generally purified by RP HPLC.

TABLE 3

| Ex. No. | D | Compound Name | HPLC time/ Conditions | M+H$^+$ |
|---|---|---|---|---|
| 18 | 4-methylpiperazin-1-yl | N-[3-Methoxy-4-(5-oxazolyl)phenyl]-N'-methyl-6-(4-methyl-1-piperazinyl)-1,3,5-triazine-2,4-diamine | 0.69/J | 397.36 |
| 19 | 4-formylpiperazin-1-yl | 4-[4-[[3-Methoxy-4-(5-oxazolyl)phenyl]amino]-6-(methylamino)-1,3,5-triazin-2-yl]-1-piperazinecarboxaldehyde | 2.85/A | 411.28 |
| 20 | morpholin-4-yl | N-[3-Methoxy-4-(5-oxazolyl)phenyl]-N'-methyl-6-(4-morpholinyl)-1,3,5-triazine-2,4-diamine | 1.51/A | 383.29 |
| 21 | 2-(CH$_2$OH)piperin-1-yl | 1-[4-[[3-Methoxy-4-(5-oxazolyl)phenyl]amino]-6-(methylamino)-1,3,5-triazin-2-yl]-2-piperidinemethanol | 1.93/A | 412.27 |
| 22 | 3-[CON(C$_2$H$_5$)$_2$] piperidin-1-yl | N,N-Diethyl-1-[4-[[3-methoxy-4-(5-oxazolyl)phenyl]amino]-6-(methylamino)-1,3,5-triazin-2-yl]-3-piperidinecarboxamide | 2.01/A | 481.40 |
| 23 | 4-OH piperidin-1-yl | 1-[4-[[3-Methoxy-4-(5-oxazolyl)phenyl]amino]-6-(methylamino)-1,3,5-triazin-2-yl]-4-piperidinol | 2.41/K | 398.30 |
| 24 | 3-OH piperidin-1-yl | (R)-1-[4-[[3-Methoxy-4-(5-oxazolyl)phenyl]-amino]-6-(methylamino)-1,3,5-triazin-2-yl]-3-piperidinol | 2.53/K | 398.30 |
| 25 | 2-C$_2$H$_5$ piperidin-1-yl | 6-(2-Ethyl-1-piperidinyl)-N-[3-methoxy-4-(5-oxazolyl)phenyl]-N'-methyl-1,3,5-triazine-2,4-diamine | 2.97/A | 410.30 |
| 26 | 2-(CONH$_2$)pyrrolidin-1-yl | 1-[4-[[3-Methoxy-4-(5-oxazolyl)phenyl]amino]-6-(methylamino)-1,3,5-triazin-2-yl]-L-prolinamide | 2.03/K | 411.28 |

TABLE 3-continued

| Ex. No. | D | Compound Name | HPLC time/ Conditions | M+H$^+$ |
|---|---|---|---|---|
| 27 | 2-(CH$_2$OCH$_3$)pyrrolidin-1-yl | (S)-6-[2-(Methoxymethyl)-1-pyrrolidinyl]-N-[3-methoxy-4-(5-oxazolyl)phenyl]-N'-methyl-1,3,5-triazine-2,4-diamine | 2.04/A | 412.34 |
| 28 | 2-(CO$_2$t-bu) pyrrolidin-1-yl | 1-[4-[[3-Methoxy-4-(5-oxazolyl)phenyl]amino]-6-(methylamino)-1,3,5-triazin-2-yl]-L-proline 1,1-dimethylethyl ester | 2.45/A | 468.43 |
| 29 | 2-(CH$_2$OH) pyrrolidin-1-yl | (R)-1-[4-[[3-Methoxy-4-(5-oxazolyl)phenyl]amino]-6-(methylamino)-1,3,5-triazin-2-yl]-2-pyrrolidinemethanol | 1.47/A | 398.32 |
| 30 | 3-(N(CH$_3$)COCH$_3$) pyrrolidin-1-yl | N-[1-[4-[[3-Methoxy-4-(5-oxazolyl)phenyl]amino]-6-(methylamino)-1,3,5-triazin-2-yl]-3-pyrrolidinyl]-N methylacetamide | 1.09/A | 439.38 |
| 31 | 2-(CH$_2$OCH$_3$) pyrrolidin-1-yl | (R)-6-[2-(Methoxymethyl)-1-pyrrolidinyl]-N-[3-methoxy-4-(5-oxazolyl)phenyl]-N'-methyl-1,3,5-triazine-2,4-diamine | 2.03/A | 412.27 |
| 32 | 3-(CH$_2$OH) piperidin-1-yl | 1-[4-[[3-Methoxy-4-(5-oxazolyl)phenyl]amino]-6-(methylamino)-1,3,5-triazin-2-yl]-3-piperidinemethanol | 1.68/A | 412.23 |
| 33 | 4-(CONH$_2$) piperidin-1-yl | 1-[4-[[3-Methoxy-4-(5-oxazolyl)phenyl]amino]-6-(methylamino)-1,3,5-triazin-2-yl]-4-piperidinecarboxamide | 0.80/A | 425.26 |
| 34 | 2-(CH$_2$CO$_2$C$_2$H$_5$)-3-oxopiperazin-1-yl | 1-[4-[[3-Methoxy-4-(5-oxazolyl)phenyl]amino]-6-(methylamino)-1,3,5-triazin-2-yl]-3-oxo-2-piperazineacetic acid ethyl ester | 2.51/K | 483.26 |
| 35 | 2,5-dimethylpyrrolidin-1-yl | 6-(2,5-Dimethyl-1-pyrrolidinyl)-N-[3-methoxy-4-(5-oxazolyl)phenyl]-N'-methyl-1,3,5-triazine-2,4-diamine | 2.60/A | 396.29 |
| 36 | 3-OH pyrrolidin-1-yl | 1-[4-[[3-Methoxy-4-(5-oxazolyl)phenyl]amino]-6-(methylamino)-1,3,5-triazin-2-yl]-3-pyrrolidinol | 0.99/A | 384.25 |
| 37 | 3-N(CH$_3$)$_2$ pyrrolidin-1-yl | (S)-6-[3-(Dimethylamino)-1-pyrrolidinyl]-N-[3-methoxy-4-(5-oxazolyl)phenyl]-N'-methyl-1,3,5-triazine-2,4-diamine | 2.09/D | 411.28 |
| 38 | 3-(NCO$_2$t-bu) pyrrolidin-1-yl | (R)-[1-[4-[[3-Methoxy-4-(5-oxazolyl)phenyl]amino]-6-(methylamino)-1,3,5-triazin-2-yl]-3-pyrrolidinyl]carbamic acid 1,1-dimethylethyl ester | 2.39/A | 483.32 |
| 39 | 3(CO$_2$CH$_3$)-4-oxopiperidin-1-yl | 1-[4-[[3-Methoxy-4-(5-oxazolyl)phenyl]amino]-6-(methylamino)-1,3,5-triazin-2-yl]-4-oxo-3-piperidinecarboxylic acid methyl ester | 2.65/A | 454.26 |

TABLE 3-continued

| Ex. No. | D | Compound Name | HPLC time/ Conditions | M+H+ |
|---|---|---|---|---|
| 40 | 2-(CH$_2$OH) pyrrolidin-1-yl | (S)-1-[4-[[3-Methoxy-4-(5-oxazolyl)phenyl]amino]-6-(methylamino)-1,3,5-triazin-2-yl]-2-pyrrolidinemethanol | 3.08/D | 398.25 |
| 41 | 2-(CH$_2$pyrrolidin-1-yl) pyrrolidin-1-yl | (S)-1-[4-[[3-Methoxy-4-(5-oxazolyl)phenyl]amino]-6-(methylamino)-1,3,5-triazin-2-yl]-2-pyrrolidinemethanol | 2.33/D | 451.32 |
| 42 | 2-(CO$_2$C$_2$H$_5$) piperidin-1-yl | 1-[4-[[3-Methoxy-4-(5-oxazolyl)phenyl]amino]-6-(methylamino)-1,3,5-triazin-2-yl]-2-piperidinecarboxylic acid ethyl ester | 2.71/A | 454.28 |
| 43 | Piperazin-1-yl | 1-[4-[[3-Methoxy-4-(5-oxazolyl)phenyl]amino]-6-(methylamino)-1,3,5-triazin-2-yl]-2-piperidinecarboxylic acid ethyl ester | 2.09/D | 383 |
| 44 | 3-amino pyrrolidin-1-yl | 1-[4-[[3-Methoxy-4-(5-oxazolyl)phenyl]amino]-6-(methylamino)-1,3,5-triazin-2-yl]-2-piperidinecarboxylic acid ethyl ester | 2.20/D | 383 |

EXAMPLE 45

6-(2-Furanyl)-N-[3-methoxy-4-(5-oxazolyl)phenyl]-N'-methyl-1,3,5-triazine-2,4-diamine

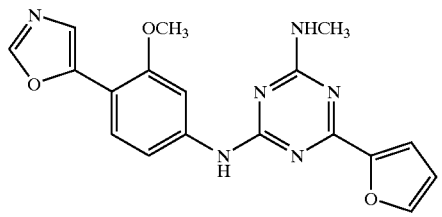

A mixture of 2-Chloro-4-methylamino-6-(4-oxazol-5-yl-3-methoxyphenylamino)triazine, 17B, (50 mg, 0.151 mmol), 2-(tributylstannyl)furan (170 mg, 0.462 mmol), Pd(PPh$_3$)$_4$ (18 mg, 0.015 mmol) and triphenylphosphine (8.1 mg, 0.03 mmol) in N-methyl-2-pyrrolidinone (2 mL) was heated to 100° C. for 28 hours. The reaction mixture was concentrated to yield a crude product that was added to 20 mL of EtOAc. The solid was removed with filtration and then the solution concentrated to give a crude product which was purified with a prep TLC plate with CH$_2$Cl$_2$. The isolated crude product was dissolved in methanol (10 mL) and stood at rt for 2 days. The solid was precipitated out and collected as the title compound (5.2 mg, 9.5%). NMR (CDCl$_3$): δ8.36 (1H, s), 7.20–8.20 (6H, m), 6.90 (1H, m), 3.97 (3H, s), 2.91 (3H, s); LC-MS: m/z 365.23 (M+H)$^+$

EXAMPLE 46

N-[3-Methoxy-4-cyanophenyl]-5-phenyl-2-oxazolamine

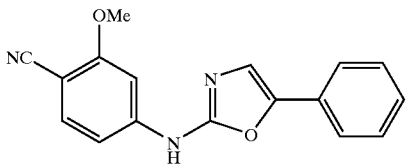

Example 46 Part A. 2-Methoxy-4-nitrobenzonitrile

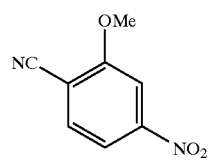

46A

Commercially available 2-Bromo-5-nitroanisole (1.0 g, 4.3 mmol), zinc cyanide (304 mg, 2.59 mmol) and Pd(PPh$_3$)$_4$ (199 mg, 0.17 mmol) was added to anhydrous DMF (6 mL) and heated at 80° C. for 4h. The reaction mixture was cooled to rt and diluted with 100 mL of toluene. The organic layer was washed with 2N ammonium hydroxide, water, and brine, dried over magnesium sulfate, filtered and concentrated under reduced pressure. The residue was recrystalized from EtOAc to yield 200 mg (26%) of the product 46A. $^1$H NMR (400 MHz) CDCl$_3$: δ8.44 (d, J=8 Hz, 1H) 7.97 (s, 1H), 7.90 (d, J=8 Hz, 1H), 4.21, (s, 3H).

Example 46 Part B. 3-Methoxy-4-cyanoaniline

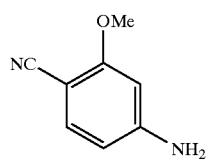

46B

Benzene derivative 46B (1.0 g, 5.62 mmol) and stannous chloride dihydrate (5.36 g, 23.7 mmol) was dissolved in a mixture of EtOH 70% (7 mL) and EtOAc (13 mL), and stirred at 70° C. for 0.5 h. The brown solution was poured onto about 100 g of crushed ice. The reaction mixture was cautiously neutralized by the portionwise addition of sodium bicarbonate. The resulting suspension was extracted with EtOAc, and the organic layer was washed with brine, dried over sodium sulfate, filtered and concentrated under reduced pressure. The residue was purified by flash column chromatography (methylene chloride MeOH 1%) to yield 786 mg, 95% of 46B. $^1$H NMR (400 MHz) CDCl$_3$: δ7.24 (d, J=8 Hz, 1H), 6.17 (d, J=8 Hz, 1H), 6.09 (s, 1H), 3.79, (s, 3H); mass spectra m/z M+H$^+$=149.1 (100%)

Example 46 Part C. N-[3-Methoxy-4-cyanophenyl]-5-2-oxazolamine

The aniline 46B was converted to the isothiocyanate in a similar manner to that described in Example 1, part E. The isothiocyanate was reacted with phenacyl azide, e.g., to a solvent such as DCM was added phenacyl azide, followed by triphenylphosphine, and 46B. The reaction mixture was stirred overnight at RT and the solid that separated out was filtered and washed with DCM to yield Example 46. MS+, 292. HPLC Retention Time: 4.140 min. Conditions: YMC S-5ODS-A, 4.6×50 mm column, 1% –100% B, linear gradient over 4 min at 4 ml/min; 1 min. isocratic at 100% B. Solvent A: 10% MeOH, 90% H$_2$O, 0.2% H$_3$PO$_4$; Solvent B: 90% MeOH, 10% H$_2$O, 0.2% H$_3$PO$_4$.

EXAMPLE 47

2-Amino-N-{2-[2-(3-methoxy-4-methyl-phenylamino)-oxazol-5-yl]-benzyl}-N-methyl-acetamide

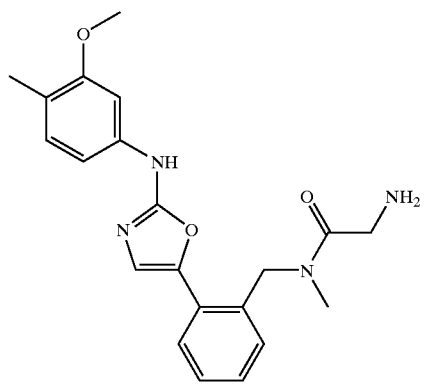

47

Example 47 Part A. (2-Bromo-benzyl)-methyl-amine

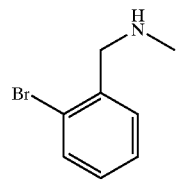

47A

A solution of 2-bromobenzylamine (9 g, 36.1 mmol) in MeOH (60 ml) was added dropwise over 30 min. to a solution of methylamine in MeOH (200 mL of a 2.0 M solution, 0.4 mol). The resulting solution was stirred at rt for 2 h and concentrated. The residue obtained was dissolved in DCM (100 mL) and successively washed with saturated aqueous sodium carbonate, dried over sodium sulphate, and concentrated. The resulting oil was distilled to afford the title compound (7 g, 95%) as a colorless oil (b.p. 110° C. at 0.1 mm Hg, LC/MS retention time=1.22 min.; M$^+$=201.92 Column: Phenominex 4.6 mm×50 mm. Solvent A=10% MeOH, 90% H$_2$O, 10 mM NH4Ac; Solvent B=90% MeOH, 10% H$_2$O, 10 nM NH4Ac, Flow rate: 4 mL/min, Gradient: 0% B–100% B 4 min.).

Example 47, Part B {[(2-Bromo-benzyl)-methyl-carbamoyl]-methyl}-carbamic acid tert-butyl Ester

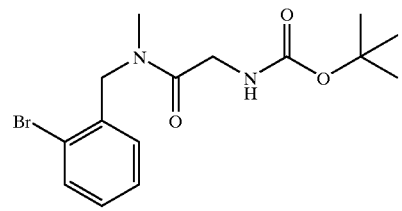

47B

To a solution of 47A (1.0 g, 5 mmol) in 50 mL of DCM was added N-Boc-glycine (950 mg, 5.4 mmol) followed by 1-hydroxy-7-azabenzotriazole (800 mg, 5.84 mmol) and 1-(3-dimethylaminopropyl)-3-ethylcarbodiimide hydrochloride (4.41 g, 7.38 mmol). The reaction mixture was stirred at RT for 4 hours and concentrated under reduced pressure. The resulting oil was dissolved in EtOAc and washed successively with saturated sodium bicarbonate, 1N-hydrochloric acid, dried over sodium sulfate and concentrated under reduced pressure to give the title compound (1.8 g, 99%) as a colorless oil, which was used as such for the subsequent step without further purification.

Example 47 Part C. ({[2-(1-Ethoxy-vinyl)-benzyl]-methyl-carbamoyl}-methyl)-carbamic acid tert-butyl ester

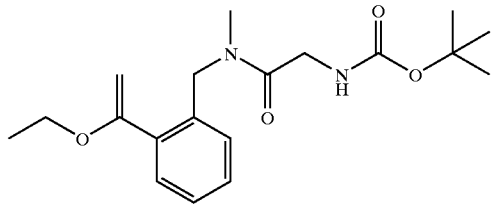

47C

To a solution of 47B (1.0 g, 2.79 mmol) in 50 mL of dioxane was added tributyl(1-ethoxyvinyl)tin (0.976 mL, 2.70 mmol) and dichlorobis(triphenyl-phosphine)palladium (II) (0.160 g, 0.16 mmol). The reaction mixture was equipped with a reflux condenser and heated at 100 ° C. for 18 hours. More dichlorobis(triphenylphosphine)palladium (II) (0.100 g, 0.10 mmol) was added and the mixture was heated at 100° C. for another 2 h. The mixture was cooled to RT, concentrated under reduced pressure and the residue obtained was taken up in EtOAc. A solution of saturated potassium fluoride was added, and the resulting mixture was filtered over a thin pad of Celite® into a separating funnel. The filtrate was washed successively with saturated potassium fluoride and water, then dried over sodium sulfate and concentrated under reduced pressure. The resulting oil was purified by silica gel column chromatography to yield the title compound as an oil (0.820 g, 84%) (LC/MS retention time=3.61 min.; $M^+$=349, Column: Phenominex 4.6 mm×50 mm, Solvent A=10% MeOH, 90% $H_2O$, 10 mM NH4Ac; Solvent B=90% MeOH, 10% $H_2O$, 10 nM NH4Ac, Flow rate: 4 mL/min, Gradient: 0% B-100% B 4 min.).

Example 47 Part D. ({[2-(2-Azido-acetyl)-benzyl]-methyl-carbamoyl}-methyl)-carbamic acid tert-butyl ester

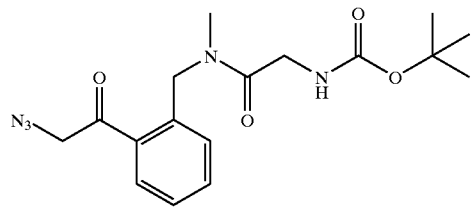

47D

To a solution of 47C (3.6 g, 10.3 mmol) in THF (30 mL) and water (5 mL) was added N-bromosuccinimide (2.0 g, 11.23 mmol) and the contents stirred at RT for 10 min. The solution was concentrated under reduced pressure and partitioned between DCM and water. The DCM layer was dried over sodium sulfate, concentrated under reduced pressure to yield ({[2-(2-Bromo-acetyl)-benzyl]-methyl-carbamoyl}-methyl)-carbamic acid tert-butyl ester, which was then dissolved in a mixture of acetone (20 mL) and water (5 mL). Sodium azide (0.737 g 11.16 mmol) was added and the reaction mixture stirred at 50° C. for 10 min., concentrated under reduced pressure and partitioned between DCM and water. The DCM layer was dried over sodium sulfate and concentrated under reduced pressure. The resulting oil was purified by silica gel column chromatography to yield the title compound as a yellow oil (2.56 g, 68%) (LC/MS retention time 2.90 min.; $M^+$=363, Column: Phenominex 4.6 mm×50 mm, Solvent A=10% MeOH, 90% $H_2O$, 10 mM NH4Ac; Solvent B=90% MeOH, 10% $H_2O$, 1 nM NH4Ac, Flow rate: 4 mL/min, Gradient: 0% B-100% B 4 min.).

Example 47 Part E. 4-Isothiocyanato-2-methoxy-1-methyl-benzene

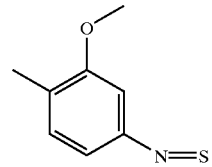

47E

To a solution of 3-methoxy-4-methylaniline (50 mg, 0.36 mmol) in DCM (2 mL) was added thiocarbonyldiimizaole (68 mg, 0.38 mmol) and the mixture was stirred at rt for 3 h. The mixture was concentrated under reduced pressure, and the residue was dissolved in MeOH (3 mL) and filtered through an SCX cartridge (CUBX1HL, 500 mg cartridge, United Chemical Technologies, Bristol Pa., USA). The filtrate was concentrated under reduced pressure to afford the title compound which was used as such for the subsequent step without further purification.

Example 47 Part F. 2-Amino-N-{2-[2-(3-methoxy-4-methyl-phenylamino)-oxazol-5-yl]-benzyl}-N-methyl-acetamide To a solution of 47D (0.126 g, 0.35 mmol) in 2 mL of dioxane was added 2E (0.066 g, 0.36 mmol) followed by triphenylphosphine (0.100 g, 0.38 mmol). The reaction mixture was placed in an oil bath preheated to 80° C. and stirred for 2 hour, then cooled to rt and the solvent was evaporated. The residue was treated for 1 h at rt with a 1:1 mixture of TFA and DCM, and the mixture was concentrated under reduced pressure. The residue was dissolved in MeOH (2 mL), loaded onto an SCX cartridge (CUBX1HL, 500 mg cartridge, United Chemical Technologies, Bristol Pa., USA) which was washed with MeOH (3 mL). The title compound was eluted from the cartridge with a 2.0 M solution of ammonia in MeOH (3 mL) and purified by preparative reverse phase HPLC to yield 0.025 g of a yellow powder. (LC/MS retention time=3.17 min.; $M^+$=381, Column: Phenominex 4.6 mm×50 mm, Solvent A=10% MeOH, 90% $H_2O$, 10 mM NH4Ac; Solvent B=90% MeOH, 10% $H_2O$, 10 nM NH4Ac, Flowrate: 4 mL/min, Gradient: 0% B-100% B 4min.).

EXAMPLE 48

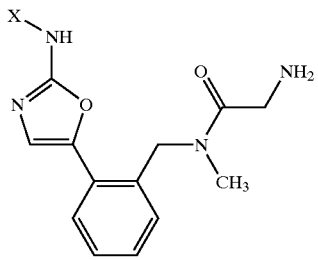

(If)

Compounds 48–67 were prepared from 47D by a route analogues to that used in Example 47 replacing 3-methoxy- 4-methylaniline with the required X—NH$_2$. The compounds of these examples have structures reflected by the above formula (If), above, wherein X is as outlined in Table 4 below.

TABLE 4

| Ex | X | Name | HPLC time (min) | M+ |
|---|---|---|---|---|
| 48 | (3-methoxyphenyl) | 2-Amino-N-{2-[2-(3-methoxy-phenylamino)-oxazol-5-yl]-benzyl}-N-methyl-acetamide | 2.5$^a$ | 367.3 |
| 49 | (phenyl) | 2-Amino-N-methyl-N-[2-(2-phenyl-amino-oxazol-5-yl)-benzyl]-acetamide | 2.37$^a$ | 337.3 |
| 50 | (3-chlorophenyl) | 2-Amino-N-{2-[2-(3-chloro-phenylamino)-oxazol-5-yl]-benzyl}-N-methyl-acetamide | 2.91$^a$ | 371.25 |
| 51 | (4-chlorophenyl) | 2-Amino-N-{2-[2-(4-chloro-phenylamino)-oxazol-5-yl]-benzyl}-N-methyl-acetamide | 2.89$^a$ | 371.23 |
| 52 | (4-methoxyphenyl) | 2-Amino-N-{2-[2-(4-methoxy-phenylamino)-oxazol-5-yl]-benzyl}-N-methyl-acetamide | 2.21$^a$ | 367.29 |
| 53 | (2,4-dichlorophenyl) | 2-Amino-N-{2-[2-(2,4-dichloro-phenylamino)-oxazol-5-yl]-benzyl}-N-methyl-acetamide | 3.07$^a$ | 405.19 |
| 54 | (3,4-dichlorophenyl) | 2-Amino-N-{2-[2-(3,4-dichloro-phenylamino)-oxazol-5-yl]-benzyl}-N-methyl-acetamide | 3.22$^a$ | 405.21 |
| 55 | (3-cyanophenyl) | 2-Amino-N-{2-[2-(3-cyano-phenylamino)-oxazol-5-yl]-benzyl}-N-methyl-acetamide | 2.56$^a$ | 362.29 |

TABLE 4-continued

| Ex | X | Name | HPLC time (min) | M+ |
|---|---|---|---|---|
| 56 | 4-cyanophenyl | 2-Amino-N-{2-[2-(4-cyano-phenylamino)-oxazol-5-yl]-benzyl}-N-methyl-acetamide | 2.55[a] | 362.29 |
| 57 | 4-tert-butylphenyl | 2-Amino-N-{2-[2-(4-tert-butyl-phenylamino)-oxazol-5-yl]-benzyl}-N-methyl-acetamide | 3.17[a] | 391.21 |
| 58 | 4-(methoxycarbonyl)phenyl | 4-[5-(2-{[(2-Amino-acetyl)-methyl-amino]-methyl}-phenyl)-oxazol-2-ylamino]-benzoic acid methyl ester | 2.72[a] | 395.29 |
| 59 | 4-nitrophenyl | 2-Amino-N-methyl-N-{2-[2-(4-nitro-phenylamino)-oxazol-5-yl]-benzyl}-acetamide | 2.74[a] | 382.29 |
| 60 | 4-acetylphenyl | N-{2-[2-(4-Acetyl-phenyl-amino)-oxazol-5-yl]-benzyl}-2-amino-N-methyl-acetamide | 2.59[b] | 379.18 |
| 61 | 3-nitrophenyl | 2-Amino-N-methyl-N-{2-[2-(3-nitro-phenylamino)-oxazol-5-yl]-benzyl}-acetamide | 2.81[b] | 382.16 |
| 62 | 4-carbamoylphenyl | 4-[5-(2-{[(2-Amino-acetyl)-methyl-amino]-methyl}-phenyl)-oxazol-2-ylamino]-benzamide | 4.45[a] | 380.23 |
| 63 | 4-butyrylphenyl | 2-Amino-N-{2-[2-(4-butyryl-phenyl-amino)-oxazol-5-yl]-benzyl}-N-methyl-acetamide | 2.99[a] | 407.28 |

TABLE 4-continued

| Ex | X | Name | HPLC time (min) | M+ |
|---|---|---|---|---|
| 64 | ![structure] | N-{2-[2-(3-Acetylamino-phenyl-amino)-oxazol-5-yl]-benzyl}-2-amino-N-methyl-acetamide | 2.2[a] | 394.23 |
| 65 | ![structure] | 3-[5-(2-{[(2-Amino-acetyl)-methyl-amino]-methyl}-phenyl)-oxazol-2-ylamino]-N-methyl-benzamide | 2.21[a] | 394.24 |
| 66 | ![structure] | N-{2-[2-(4-Acetylamino-phenylamino)-oxazol-5-yl]-benzyl}-2-amino-N-methyl-acetamide | 2.08[a] | 394.24 |
| 67 | ![structure] | 4-[5-(2-{[(2-Amino-acetyl)-methyl-amino]-methyl}-phenyl)-oxazol-2-ylamino]-2-methoxy-benzoic acid methyl ester | 2.72[a] | 425.2 |

HPLC Conditions: The HPLC conditions for the examples listed above is as follows:
[a]Column: Phenominex Luna C18 4.6 × 5.0 mm. Solvent A = 10% MeOH, 90% $H_2O$, 0.1% TFA; Solvent B = 90% MeOH, 10% $H_2O$, 0.1% TFA. Flow rate: 4 mL/min. Gradient: 4 min 0%B–100%B.
[b]Column: Phenominex ODS 4.6 × 5.0 mm. Solvent = 10% MeOH, 90% $H_2O$, 0.1% TFA; Solvent B = 90% MeOH, 10% $H_2O$, 0.1% TFA. Flow rate: 4 mL/min. Gradient: 4 min 0%B–100%B.

EXAMPLE 68

2-Amino-N-{3-[2-(3-methoxy-4-oxazol-5-yl-phenylamino)-oxazol-5-yl]-pyridin-4-ylmethyl}-N-methyl-acetamide

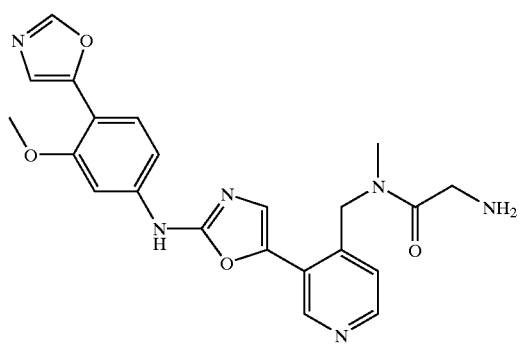

Step A

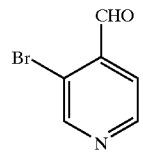

68A

A solution of n-BuLi in hexane (1.6M, 11.8 ml, 18.9 mmol) was added to a solution of DIA (3.18 ml, 22.7 mmol) in THF (40 ml) at −78° C. under nitrogen. The resulting solution was stirred at −78° C. for 1 h. To the mixture was added 3-bromopyridine (2.0 g, 12.6 mmol) dropwise at −78° C. After stirring at −78° C. for 1 h, DMF (4.78 ml, 63 mmol) was added dropwise. The mixture was stirred at −78° C. for 1 h, warmed to rt and stirred at rt overnight. The reaction was quenched with the addition of saturated $NH_4Cl$ solution. The product was extracted with $Et_2O$, washed with brine, dried ($MgSO_4$) and concentrated to give the crude product. Purification by flash chromatography (silica, 20–30% EtOAc/hexane) gave 68A as white crystals.

Step B

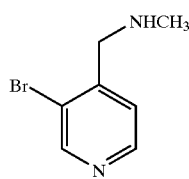
68B

To a solution of 68A (557 mg, 2.99 mmol) in MeOH (5.0 ml) at 0° C. was added a solution of $CH_3NH_2$ (2 N, 10 ml) in MeOH. The mixture was stirred at rt for 1 h, cooled to 0° C., and $NaBH_4$ (566 mg) was added. The reaction was stirred at rt for 3 days, quenched with water (a few drops). The solvent was removed and the residue partitioned between EtOAc and brine. The organic layer was separated, washed with brine, dried ($MgSO_4$) and concentrated to give 68B (544 mg) as a colorless oil.

Step C

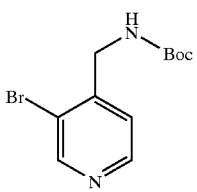
68C

To a solution of 68B (544 mg, 2.7 mmol) in DCM (15 ml) at rt was added $(Boc)_2O$ (684 μl) slowly. The mixture was stirred at rt for 2 h. The solvent was removed and the residue was purified by flash chromatography (silica, 10–25% EtOAc/hexane) to give 68C (700 mg) as a light yellow oil.

Step D

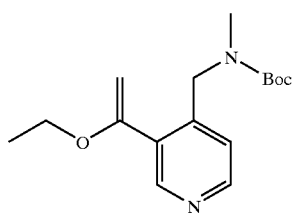
68D

A mixture of 68C (600 mg, 2.0 mmol), tributyl (1-ethoxyl vinyl)tin (887 μl), $PdCl_2(PPh_3)_2$ (140 mg) in dioxane (4 ml) was heated at 95–100 ° C. for 4 h. The mixture was filtered through a layer of celite and concentrated to give the crude product which was purified by flash chromatography (silica, 20% EtOAc/hexane) to give 68D (572 mg) as a yellow oil. LC-MS $(M+H)^+293$.

Step E

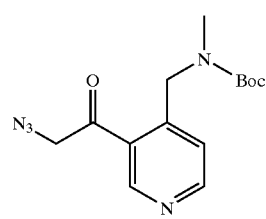
68E

To a solution of 68D (210 mg, 0.72 mmol) in THF/$H_2O$ (3:1, 2.0 ml) at rt was added NBS (140 mg). The mixture was stirred at rt for 30 min and $NaN_3$ (51 mg) was added. The mixture was stirred at rt for 2 h. The solvent was removed and the residue was partitioned between EtOAc and water. The organic layer was separated, washed with brine, dried ($MgSO_4$) and concentrated to give 68E (250 mg) as a brown solid. LC-MS $(M+H)^+306$.

Step F

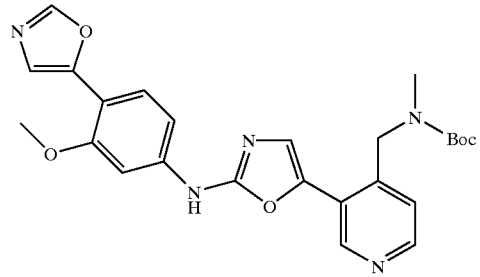
68F

A mixture of 68E (73%, 98 mg, 0.23 mmol), isothiocyanate 2E (59 mg, 0.25 mmol) and $PPh_3$-polymer bound (3 mmol/g, 160 mg, 0.48 mmol) in dioxane (2 ml) was heated at 90 ° C. for 1 h. The mixture was filtered through a layer of celite and concentrated to give the crude product which was purified by flash chromatography (silica, EtOAc) to give 68F (52 mg) as a yellow solid.

Step G

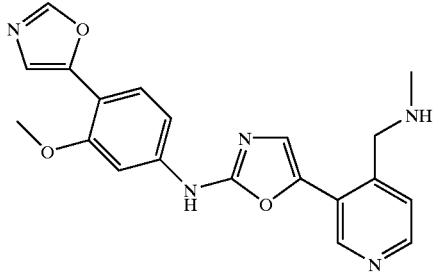
(68G)

To a solution of 68F (51 mg, 0.11 mmol) in DCM (1.5 ml) at rt was added TFA (500 μl). The mixture was stirred at rt for 3 h. Removal of solvent and TFA gave 68G as a yellow film.

Step H

EXAMPLE 68

A mixture of 68G, Boc-glycine (23 mg, 0.13 mmol), DIPEA (191 μl), EDC (25 mg), HOAt (18 mg) in DCM (3 ml) was stirred at rt overnight. The solvent was removed and the residue treated with 20% TFA/DCM (2 ml) at rt for 2 h.

The solvent was removed and the residue purified by RP HPLC to give Example 68 (11 mg, TFA salt). LC-MS (M+H)$^+$435.

EXAMPLE 69

2-Amino-N-{2-[2-(3-methoxy-4-oxazol-5-yl-phenylamino)-oxazol-5-yl]-pyridin-3-ylmethyl}-N-methyl-acetamide

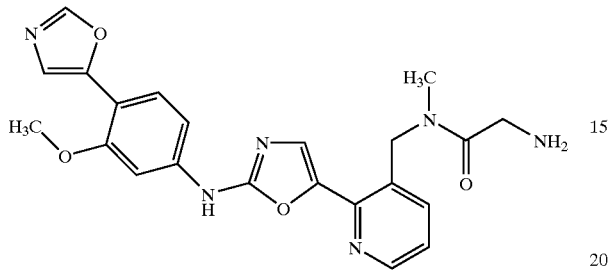

The procedure described for Example 68 was followed using 2-bromopyridine to obtain Example 69 as yellow fluffy powder after purification by RP HPLC. LC-MS (M+H)$^+$435.

Although the present invention has been described in some detail by way of illustration and example for purposes of clarity and understanding, it will be apparent that certain changes and modifications may be practiced within the scope of the appended claims. All examples are illustrative of the present invention and are not to be construed as limiting of the scope or embodiments of the appended claims.

We claim:

1. A compound of the formula,

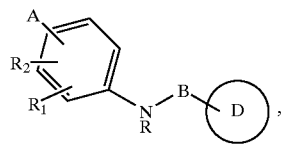

or a pharmaceutically-acceptable salt, hydrate or prodrug thereof, wherein:

D is a monocyclic or bicyclic carbocyclic ring system optionally substituted by one to four $(CR^9R^{10})_n E$ groups;

$R^4$ is selected from hydrogen, halogen, $NO_2$, $CF_3$, $C_0$-$C_4$ alkylCN, $C_1$-$C_4$alkoxy-, $C_0$-$C_4$ alkylhydroxy, $C_1$-$C_4$ alkyl-, $C_1$-$C_4$ alkylcarbonyl-, $C_0$-$C_4$ alkylOCOR$^6$, $C_0$-$C_4$ alkylOC(=O)OR$^6$, $C_0$-$C_4$ alkylOC(=O)NR$^6$R$^7$, $C_0$-$C_4$ alkylNR$^6$R$^7$, $C_0$-$C_4$alkylNR$^7$C(=O)OR$^6$, $C_0$-$C_4$ alkylNR$^6$SO$_2$NR$^6$R$^7$, $C_0$-$C_4$ alkylNR$^6$SO$_2$R$^7$, $C_0$-$C_4$ alkylSR$^6$, $C_0$-$C_4$ alkylS(O)R$^7$, $C_0$-$C_4$ alkylSO$_2$R$^7$, SO$_3$R$^7$, $C_0$-$C_4$ alkylSO$_2$NR$^6$R$^7$, $C_0$-$C_4$alkyl SO$_2$NR$^7$CO(CR$^9$R$^{10}$)$_q$R$^6$, $C_0$-$C_4$ alkylCO$_2$R$^6$, $C_0$-$C_4$ alkylC(=O)NR$^6$R$^7$, and $C_0$-$C_4$alkyl C(=O)NR$^6$SO$_2$(CR$^9$R$^{10}$)$_q$R$^7$;

R is hydrogen or $C_1$-$C_4$alkyl;

$R^1$ and $R^2$ are each independently selected from hydrogen, halogen, $NO_2$, $C_1$-$C_4$alkyl, $C_3$-$C_{10}$ cycloalkyl, $C_2$-$C_6$alkenyl, $C_2$-$C_6$alkynyl, haloalkyl, haloalkoxy, OR$^6$, O(CR$^9$R$^{10}$)$_r$CO$_2$R$^6$, O(CR$^9$R$^{10}$)$_m$ NR$^6$R$^7$, O(CR$^9$R$^{10}$)$_p$CN, O(CR$^9$R$^{10}$)$_r$C(=O)NR$^6$R$^7$, $C_1$-$C_4$alkylcarbonyl, CN, NR$^6$R$^7$, NR$^7$(CR$^9$R$^{10}$)$_r$ CO$_2$R$^6$, NR$^7$OR$^6$, NR$^7$(CR$^9$R$^{10}$)$_m$OR$^6$, NR$^7$CH[(CR$^9$R$^{10}$)$_p$OR$^6$]$_2$, NR$^7$C[(CR$^9$R$^{10}$)$_p$OR$^6$]$_3$, NR$^7$(CR$^9$R$^{10}$)$_m$OR$^6$, NR$^7$(CR$^9$R$^{10}$)$_m$NR$^6$R$^7$, NR$^6$(CR$^9$R$^{10}$)$_m$ SO$_2$(CR$^9$R$^{10}$)$_q$R$^7$, SR$^7$, S(O)R$^7$, SO$_2$R$^7$, SO$_2$NR$^6$, SO$_3$R$^7$, CO$_2$R$^6$, and C(=O)NR$^6$R$^7$; or, alternatively, $R^1$ and $R^2$, when on adjacent carbon atoms, may be taken together to be methylenedioxy or ethylenedioxy;

$R^6$, $R^7$ and $R^8$ are each independently selected from hydrogen, $C_1$-$C_6$alkyl, $C_3$-$C_{10}$ cycloalkyl, $C_2$-$C_6$alkenyl, $C_2$-$C_6$alkynyl, $C_1$-$C_6$ alkylcarbonyl, $C_3$-$C_7$ cycloalkyl($C_0$-$C_5$alkyl)carbonyl, $C_1$-$C_6$ alkoxycarbonyl, aryl($C_0$-$C_5$ alkyl)carbonyl, aryl ($C_1$-$C_5$ alkoxy)carbonyl, heterocyclic($C_0$-$C_5$ alkyl) carbonyl, heterocyclic($C_1$-$C_5$ alkoxy)carbonyl, $C_1$-$C_6$alkylsulfonyl, arylsulfonyl, heteroarylsulfonyl, $C_0$-$C_4$alkylaryl, $C_0$-$C_4$alkylheterocyclic, wherein said cycloalkyl, aryl or heterocyclic groups are substituted with 0–2 substituents independently selected from the group consisting of $C_1$-$C_4$alkyl, hydroxy, $C_1$-$C_4$ alkoxy, F, Cl, Br, haloalkyl, NO$_2$ and CN; ; provided, however, that when directly attached to a sulfonyl group as in S(O)R$^7$, SO$_2$R$^7$, SO$_2$NR$^6$, or SO$_3$R$^7$, then $R^7$ is not hydrogen;

or, alternatively, $R^6$ and $R^7$, or $R^6$ and $R^8$, or $R^7$ and $R^8$, when both substituents are on the same nitrogen atom [as in (—NR$^6$R$^7$) or (—NR$^7$R$^8$)], can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo[3,2,2]nonan-3-yl, and 1-tetrazolyl, said heterocycle being optionally substituted with 0–3 groups selected from oxo, $C_0$-$C_4$alkylOH, $C_0$-$C_4$alkylOC$_1$-$C_4$alkyl, $C_0$-$C_4$alkylC(=O)NH$_2$, $C_0$-$C_4$alkylCO$_2$C$_0$-$C_4$alkyl, $C_1$-$C_6$ alkyl, $C_1$-$C_4$ alkoxy, $C_3$-$C_7$ cycloalkyl, —$C_0$-$C_6$ alkylcarbonyl, $C_3$-$C_7$ cycloalkylcarbonyl, $C_1$-$C_6$ alkoxycarbonyl, $C_3$-$C_7$ cycloalkoxycarbonyl, —NHCOalkyl, aryl, heteroaryl, arylalkoxycarbonyl, heteroarylalkoxycarbonyl, $C_1$-$C_6$ alkylsulfonyl, arylsulfonyl and heteroarylsulfonyl;

B is a 5-membered heterocycle containing one N and additional 0–3 heteroatoms selected from N, O, and S, and wherein B is optionally substituted by one to four $R^{11}$ groups;

$R^9$ hydrogen or $C_1$-$C_4$alkyl;

$R^{10}$ is selected from hydrogen or $C_1$-$C_4$ alkyl, $C_1$-$C_4$ alkylhydroxy, $C_1$-$C_4$alkylaryl or $C_1$-$C_4$alkylheteroaryl, wherein said aryl or heteroaryl group may be substituted with 0–3 groups independently selected from hydrogen, halogen, NO$_2$, $C_1$-$C_4$alkyl, $C_3$-$C_{10}$ cycloalkyl, $C_2$-$C_6$alkenyl, $C_2$-$C_6$alkynyl, haloalkyl, haloalkoxy, OH, $C_1$-$C_4$alkoxy, $C_1$-$C_4$alkylcarbonyl, CN, NR$^6$R$^7$, SR$^6$, S(O)R$^7$, SO$_2$R$^7$, SO$_3$R$^7$, SO$_2$NR$^6$, CO$_2$R$^6$, and C(=O) NR$^6$R$^7$;

$R^{11}$ is selected from hydrogen, halogen, NO$_2$, $C_1$-$C_4$alkyl, $C_3$-$C_{10}$ cycloalkyl, $C_2$-$C_6$alkenyl, $C_2$-$C_6$alkynyl, haloalkyl, haloalkoxy, $C_1$-$C_4$alkoxy-, OR$^6$, O(CR$^9$R$^{10}$)$_r$CO$_2$R$^6$, O(CR$^9$R$^{10}$)$_m$ NR$^6$R$^7$, O(CR$^9$R$^{10}$)$_p$CN, O(CR$^9$R$^{10}$)$_r$C(=O)NR$^6$R$^7$, $C_1$-$C^4$alkylcarbonyl-, CN, NR$^6$R$^7$, NR$^7$(CR$^9$R$^{10}$)$_r$ CO$_2$R$^6$, NR$^7$OR$^6$, NR$^7$(CR$^9$R$^{10}$)$_m$OR$^6$, NR$^7$CH[(CR$^9$R$^{10}$)$_p$OR$^6$]$_2$, NR$^7$C[(CR$^9$R$^{10}$)$_p$OR$^6$]$_3$, NR$^7$C (=O)R⁶, NR⁷(CR⁹R¹⁰)ₘOR⁶, NR⁷(CR⁹R¹⁰)ₘNR⁶R⁷, NR⁶(CR⁹R¹⁰)ₘSO₂(CR⁹R¹⁰)qR⁷, SR⁷, S(O)R⁷, SO₂R⁷, SO₂NR⁶, SO₃R⁷, CO₂R⁶, and C(=O)NR⁶R⁷;

E is selected from hydrogen, halogen, NO₂, C₁–C₄alkyl, C₃–C₁₀ cycloalkyl, C₂–C₆alkenyl, C₂–C₆ alkynyl, haloalkyl, haloalkoxy, OR⁶, CN, CHO, CO₂R⁶, C(=O)NR⁶R⁷, OCOR⁶, OC(=O)OR⁶, OC(=O)NR⁶R⁷, OCH₂CO₂R⁶, C(=O)R⁶, NR⁶R⁷, NR⁷C(=O)R⁶, NR⁷C(=O)OR⁶, NR⁷C(=O)C(=O)OR⁶, NR⁷C(=O)C(=O)NR⁶R⁷, NR⁷C(=O)C(=O)(C₁–C₆alkyl), NR⁷C(=NCN)OR⁶, NR⁷C(=O)NR⁶R⁷, NR⁷C(=NCN)NR⁶R⁷, NR⁷C(=NR⁶)NR⁷R⁸, NR⁶SO₂NR⁶R⁷, NR⁶SO₂R⁷, SR⁶, S(=O)R⁷, SO₂R⁷, SO₃R⁷, SO₂NR⁶R⁷, NHOR⁶, NR⁶NR⁷NR⁸, N(COR⁶)OH, N(CO₂R⁶)OH, CO₂R⁶, C(=O)NR⁷(CR⁹R¹⁰)ᵣR⁶, CO(CR⁹R¹⁰)pO(CHR⁹)qCO₂R⁶, CO(CR⁹CR¹⁰)ᵣOR⁶, CO(CR⁹R¹⁰)pO(CR⁹R¹⁰)ᵣR⁶, CO(CR⁹CR¹⁰)ᵣNR⁶R⁷, OC(O)O(CR⁹R¹⁰)ₘNR⁶R⁷, O(CO)N(CR⁹R¹⁰)ᵣR⁶, O(CR⁹R¹⁰)ₘNR⁶R⁷, NR⁷C(O)(CR⁹R¹⁰)ᵣR⁶, NR⁷C(O)(CR⁹R¹⁰)ᵣOR⁶, NR⁷C(=NC)(CR⁹R¹⁰)ᵣR⁶, NR⁷CO(CR⁹R¹⁰)ᵣNR⁶R⁷, NR⁷(CR⁹R¹⁰)ₘOR⁶, NR⁷(CR⁹R¹⁰)ᵣCO₂R⁶, NR⁷(CR⁹R¹⁰)ₘNR⁶R⁷, NR⁶(CR⁹R¹⁰)ₘSO₂(CR⁹R¹⁰)ₛR⁷, C(=O)NR⁶(CR⁹R¹⁰)ₙSO₂(CR⁹R¹⁰)qR⁷, SO₂NR⁷(CR⁹R¹⁰)ₙCO(CR⁹R¹⁰)qR⁶, SO₂NR⁶(CR⁹R¹⁰)ₘOR⁶, C₃–C₁₀ cycloalkylmethyl, aryl, heterocyclic and alkylaryl, wherein said aryl groups may be substituted with 0–2 substituents independently selected from R¹²;

R¹² at each occurrence is independently selected from hydrogen, halogen, NO₂, C₁–C₄alkyl, C₃–C₁₀ cycloalkyl, C₂–C₆alkenyl, C₂–C₆alkynyl, haloalkyl, haloalkoxy, oxo, OR⁶, O(CR⁹R¹⁰)ᵣCO₂R⁶, O(CR⁹R¹⁰)ₘ NR⁶R⁷, O(CR⁹R¹⁰)pCN, O(CR⁹R¹⁰)ᵣC(=O)NR⁶R⁷, C₁–C₄alkylcarbonyl-, CN, NR⁶R⁷, NR⁷(CR⁹R¹⁰)ᵣCO₂R⁶, NR⁷OR⁶, NR⁷(CR⁹R¹⁰)ₘOR⁶, NR⁷CH[(CR⁹R¹⁰)pOR⁶]₂, NR⁷C[(CR⁹R¹⁰)pOR⁶]₃, NR⁷C(=O)R⁶, NR⁷(CR⁹R¹⁰)ₘOR⁶, NR⁷(CR⁹R¹⁰)ₘNR⁶R⁷, NR⁶(CR⁹R¹⁰)ₘSO₂(CR⁹R¹⁰)qR⁷, SR⁷, S(O)R⁷, SO₂R⁷, SO₂NR⁶, SO₃R⁷, CO₂R⁶, and C(=O)NR⁶R⁷;

n is an integer having a value from 0–4;
m is an integer having a value from 2–6;
p is an integer having a value from 1–3;
q is an integer having a value from 0–3; and
r is an integer having a value from 0–6.

2. A compound according to claim 1, or a pharmaceutically-acceptable salt, hydrate or prodrug thereof, wherein:

D is a monocyclic or bicyclic carbocyclic ring system optionally substituted by one to two (CR⁹R¹⁰)ₙE groups;

R⁴ is selected from hydrogen, halogen, NO₂, CF₃, C₀–C₄ alkylCN, C₁–C₄alkoxy-, C₀–C₄ alkylhydroxy, C₁–C₄ alkyl-, C₁–C₄ alkylcarbonyl-, C₀–C₄alkylOCOR⁶, C₀–C₄ alkylNR⁶R⁷, C₀–C₄ alkylNR⁷C(=O)OR⁶, C₀–C₄ alkylCO₂R⁶, and C₀–C₄ alkylC(=O)NR⁶R⁷;

R is hydrogen or C₁–C₄alkyl;

R⁹ and R¹⁰ are selected from hydrogen and C₁–C₄ alkyl;

R¹ is hydrogen, halogen, NO₂, C₁–C₄alkyl, C₃–C₇cycloalkyl, C₂–C₆alkenyl, haloalkyl, haloalkoxy, OR⁶, O(CR⁹R¹⁰)ₘNR⁶R⁷, O(CR⁹R¹⁰)pCN, O(CR⁹R¹⁰)ᵣC(=O)NR⁶R⁷, C₁–C₄alkylcarbonyl-, CN, NR⁶R⁷, NR⁷(CR⁹R¹⁰)ᵣCO₂R⁶, NR⁷OR⁶, NR⁷(CR⁹R¹⁰)ₘOR⁶, NR⁷(CR⁹R¹⁰)ₘOR⁶, CO₂R⁶, or C(=O)NR⁶R⁷;

E is selected from hydrogen, halogen, NO₂, C₁–C₄alkyl, C₃–C₇cycloalkyl, C₂–C₆alkenyl, haloalkyl, haloalkoxy, OR⁶, CN, CO₂R⁶, C(=O)NR⁶R⁷, OCH₂CO₂R⁶, C(=O)R⁶, NR⁶R⁷, NR⁷C(=O)R⁶, NR⁷C(=O)NR⁶R⁷, NR⁶SO₂NR⁶R⁷, NR⁶SO₂R⁷, NHOR⁶, NR⁷C(O)(CR⁹R¹⁰)ᵣR⁶, NR⁷C(O)(CR⁹R¹⁰)ᵣOR⁶, NR⁷CO(CR⁹R¹⁰)ᵣNR⁶R⁷, NR⁷(CR⁹R¹⁰)ₘOR⁶, NR⁷(CR⁹R¹⁰)ᵣCO₂R⁶, NR⁷(CR⁹R¹⁰)ₘNR⁶R⁷, C₃–C₁₀cycloalkylmethyl, aryl, heterocyclic and C₁–C₄alkylaryl;

R⁶ and R⁷ are each independently selected from hydrogen, C₁–C₄alkyl, C₃–C₇cycloalkyl, C₂–C₆alkenyl, C₁–C₄alkylcarbonyl, C₃–C₇cycloalkyl (C₀–C₅ alkyl)carbonyl, C₁–C₄alkoxycarbonyl, aryl (C₀–C₄alkyl)carbonyl, aryl(C₁–C₄ alkoxy)carbonyl, heterocyclic(C₀–C₄alkyl)carbonyl, heterocyclic(C₁–C₄ alkoxy)carbonyl, C₀–C₄alkylaryl, C₀–C₄alkylheterocyclic, wherein said cycloalkyl, aryl or heterocyclic groups are substituted with 0–2 substituents independently selected from C₁–C₄alkyl, hydroxy, C₁–C₄ alkoxy, F, Cl, Br, haloalkyl, NO₂ and CN;

or, alternatively, R⁶ and R⁷ taken together with the nitrogen atom to which they are attached to form a heterocycle selected from 1-piperidinyl, 1-morpholinyl, 1-pyrrolidinyl, thiamorpholinyl, thiazolidinyl, 1-piperazinyl, 1-imidazolyl, and 1-tetrazolyl, said heterocycle being optionally substituted with 0–2 groups selected from oxo, C₀–C₄alkylOH, C₀–C₄alkylOC₁–C₄alkyl, C₀–C₄alkylC(=O)NH₂, C₀–C₄alkylCO₂C₁–C₄alkyl, C₁–C₆alkyl, C₁–C₄ alkoxy, C₃–C₇cycloalkyl, —C₀–C₄alkylcarbonyl, C₁–C₆ alkoxycarbonyl, —NHCOalkyl, aryl, and heteroaryl;

R¹¹ is selected from hydrogen, halogen, NO₂, C₁–C₄alkyl, C₃–C₁₀ cycloalkyl, C₂–C₆alkenyl, C₂–C₆alkynyl, haloalkyl, haloalkoxy, OR⁶, O(CR⁹R¹⁰)ᵣ CO₂R⁶, O(CR⁹R¹⁰)ₘNR⁶R⁷, O(CR⁹R¹⁰)pCN, O(CR⁹R¹⁰)ᵣC(=O)NR⁶R⁷, C₁–C₄alkylcarbonyl-, CN, NR⁶R⁷, NR⁷(CR⁹R¹⁰)ᵣCO₂R⁶, NR⁷OR⁶, NR⁷(CR⁹R¹⁰)ₘOR⁶, NR⁷CH[(CR⁹R¹⁰)pOR⁶]₂, NR⁷C[(CR⁹R¹⁰)pOR⁶]₃, NR⁷C(=O)R⁶, NR⁷(CR⁹R¹⁰)ₘOR⁶, NR⁷(CR⁹R¹⁰)ₘNR⁶R⁷, NR⁶(CR⁹R¹⁰)ₘSO₂(CR⁹R¹⁰)qR⁷, SR⁷, S(O)R⁷, SO₂R⁷, SO₂NR⁶, SO₃R⁷, CO₂R⁶, and C(=O)NR⁶R⁷;

m is an integer having a value from 2–4;
n is an integer having a value from 0–4; and
r is an integer having a value from 0–4.

3. A compound according to claim 1, or a pharmaceutically-acceptable salt, hydrate, or prodrug thereof, in which B is a five-membered unsaturated monocyclic heterocyclic ring selected from:

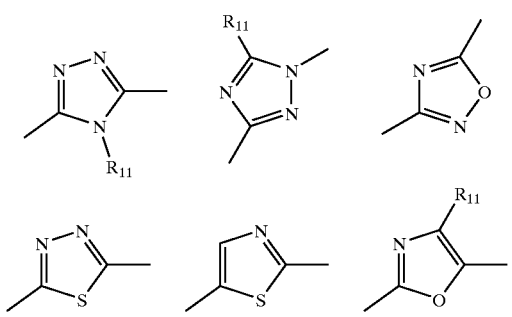

-continued

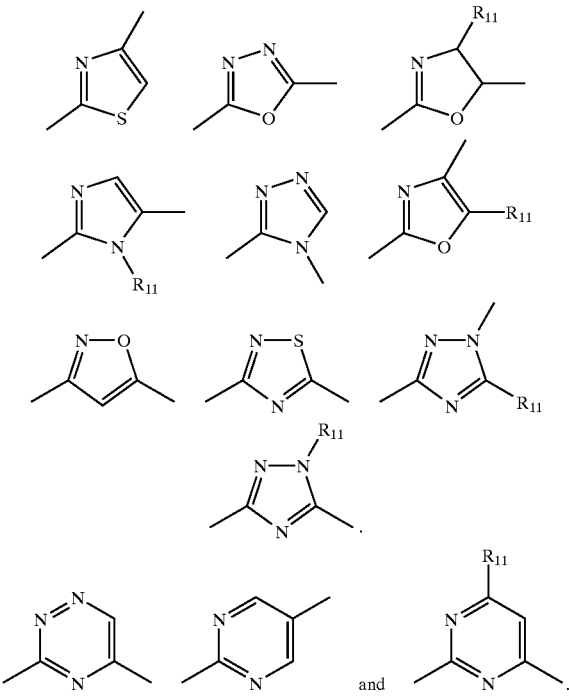

4. A compound according to claim 3, or a pharmaceutically-acceptable salt, hydrate, or prodrug thereof, in which $R^{11}$ is selected from hydrogen, halogen, $NO_2$, $C_1$–$C_4$alkyl, haloalkyl, haloalkoxy, $C_1$–$C_4$alkoxy-, $C_1$–$C_4$alkylcarbonyl-, CN, OH, $NH_2$, $NH(C_{1-4}alkyl)$, and $N(alkyl)_2$.

5. A compound according to claim 1, or a pharmaceutically-acceptable salt, hydrate, or prodrug thereof, in which B is oxazolyl.

6. A compound according to claim 1, or a pharmaceutically-acceptable salt, hydrate, or prodrug thereof, in which:
   $R^1$ is selected from hydrogen, halogen, $C_1$–$C_4$alkyl, halo$C_{1-4}$alkyl, halo $C_{1-4}$alkoxy, $O(C_{1-4}alkyl)$, CN, $NH_2$, $NH(C_{1-4}alkyl)$, and $N(C_{1-4}alkyl)_2$; and
   $R^4$ is selected from hydrogen, halogen, $NO_2$, $CF_3$, $C_0$–$C_4$ alkylCN, $C_1$–$C_4$alkoxy, $C_0$–$C_4$ alkylhydroxy, $C_1$–$C_4$ alkyl, $C(=O)(C_{1-4}alkyl)$, $CO_2(C_{1-4}alkyl)$, $NHCO_2(C_{1-4}alkyl)$, $NHC(=O)(C_{1-4}alkyl)$, $C(=O)NH_2$, $C(=O)NH(C_{1-4}alkyl)$, $C_0$–$C_4$ alkyl $NH_2$, $C_0$–$C_4$ alkyl $NH(C_{1-4}alkyl)$ and $C_0$–$C_4$ alkyl $N(C_{1-4}alkyl)_2$.

7. A compound according to claim 1, or a pharmaceutically-acceptable salt, hydrate, or prodrug thereof, in which
   E is selected from hydrogen, halogen, $NO_2$, $C_1$–$C_4$alkyl, $C_3$–$C_7$cycloalkyl, $C_2$–$C_6$alkenyl, haloalkyl, haloalkoxy, $OR^6$, CN, $CO_2R^6$, $C(=O)NR^6R^7$, $OCH_2CO_2R^6$, $C(=O)R^6$, $NR^6R^7$, $NR^7C(=O)R^6$, $NR^7C(=O)NR^6R^7$, $NR^6SO_2NR^6R^7$, $NR^6SO_2R^7$, $NHOR^6$, $NR^7C(O)(CR^9R^{10})_rR^6$, $NR^7C(O)(CR^9R^{10})_rOR^6$, $NR^7CO(CR^9R^{10})_rNR^6R^7$, $NR^7(CR^9R^{10})_mOR^6$, $NR^7(CR^9R^{10})_rCO_2R^6$, $NR^7(CR^9R^{10})_mNR^6R^7$, $C_3$–$C_{10}$cycloalkylmethyl, aryl, hetefocyclic and $C_1$–$C_4$alkylaryl;
   $R^9$ and $R^{10}$ are selected from hydrogen and $C_1$–$C_4$ alkyl; and
   $R^{11}$ is selected from hydrogen, halogen, $NO_2$, $C_1$–$C_4$alkyl, $C_3$–$C_{10}$cycloalkyl, haloalkyl, haloalkoxy, $OR^6$, CN, $NR^6R^7$, $NR^7(CR^9R^{10})_rCO_2R^6$, $NR^7OR^6$, $NR^7(CR^9R^{10})_mOR^6$, $NR^7CH[(CR^9R^{10})_pOR^6]_2$, $NR^7C(=O)R^6$, $NR^7(CR^9R^{10})_mOR^6$, $NR^7(CR^9R^{10})_mNR^6R^7$, $NR^6(CR^9R^{10})_qR^7$, $CO_2R^6$, and $C(=O)NR^6R^7$.

8. A compound according to claim 7, or a pharmaceutically-acceptable salt, hydrate, or prodrug thereof, in which:
   $R^6$ and $R^7$ are each independently selected from hydrogen, $C_1$–$C_4$alkyl, $C_3$–$C_7$cycloalkyl, $C_2$–$C_6$alkenyl, $C_1$–$C_4$alkylcarbonyl, $C_1$–$C_4$alkoxycarbonyl, $C_0$–$C_4$alkylaryl, $C_0$–$C_4$alkylheterocyclic, wherein said cycloalkyl, aryl or heterocyclic groups are substituted with 0–2 substituents independently selected from the group consisting of $C_1$–$C_4$alkyl, hydroxy, $C_1$–$C_4$ alkoxy, F, Cl, Br, haloalkyl, $NO_2$ and CN; or, alternatively, $R^6$ and $R^7$ can be taken together with the nitrogen atom to which they are attached to form a heterocycle selected from 1-piperidinyl, 1-morpholinyl, 1-pyrrolidinyl, thiamorpholinyl, thiazolidinyl, 1-piperazinyl, 1-imidazolyl, and 1-tetrazolyl, said heterocycle being optionally substituted with 0–3 groups selected from $C_0$–$C_4$alkylOH, $C_0$–$C_4$alkylO$C_1$–$C_4$alkyl, $C_0$–$C_4$alkylC$(=O)NH_2$, $C_0$–$C_4$alkylCO$_2C_0$–$C_4$alkyl, and $C_1$–$C_6$ alkyl.

9. A compound according to claim 1, or a pharmaceutically-acceptable salt thereof, in which E at least one occurrence is $NHC(=O)(CH_2)_rNR^6R^7$ or $N(alkyl)C(=O)(CH_2)_rNR^6R^7$.

10. A compound according to claim 9, or a pharmaceutically-acceptable salt, hydrate or prodrug thereof, having the formula:

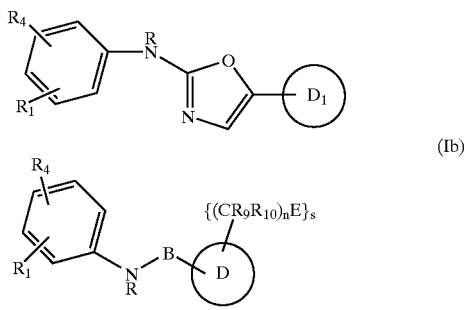

(Ib)

wherein: D is a monocyclic or bicyclic carbocyclic ring system optionally substituted by one to two $(CR^9R^{10})_nE$ groups.

11. A compound according to claim 1 which is selected from:
N-[3-Methoxy-4-cyanophenyl]-5-phenyl-2-oxazolamine;
2-Amino-N-{2-[2-(3methoxy-4-methyl-phenylamino)-oxazol-5-yl]-benzyl}-N-methyl-acetamide;
2-Amino-N-{2-[2-(3-methoxy-phenylamino)-oxazol-5-yl]-benzyl}-N-methyl-acetamide;
2-Amino-N-methyl-N-[2-(2-phenylamino-oxazol-5-yl)-benzyl]-acetamide;
2-Amino-N-{2-[2-(3-chloro-phenylamino)-oxazol-5-yl]-benzyl}-N-methyl-acetamide;
2-Amino-N-methyl-{2-[2-(4-chloro-phenylamino)-oxazol-5-yl]-benzyl}-N-methyl-acetamide;
2-Amino-N-{2-[2-(4-methoxy-phenylamino)-oxazol-5-yl]-benzyl}-N-methyl-acetamide;
2-Amino-N-{2-[2-(2,4-dichloro-phenylamino)-oxazol-5-yl]-benzyl}-N-methyl-acetamide;
2-Amino-N-{2-[2-(3,4-dichloro-phenylamino)-oxazol-5-yl]-benzyl}-N-methyl-acetamide;

2-Amino-N-{2-[2-(3-cyano-phenylamino)-oxazol-5-yl]-benzyl}-N-methyl-acetamide;

2-Amino-N-{2-[2-(4-cyano-phenylamino)-oxazol-5-yl]-benzyl}-N-methyl-acetamide;

2-Amino-N-{2-[2-(4tert-butyl-phenylamino)-oxazol-5-yl]-benzyl}-N-methyl-acetamide;

4-[5-(2-{[(2-Amino-acetyl)-methyl-amino]-methyl}-phenyl)-oxazol-2-ylamino]-benzoic acid methyl ester;

2-Amino-N-methyl-N-{2-[2-(4-nitro-phenylamino)-oxazol-5-yl]-benzyl}-acetamide;

N-{2-[2-(4-Acetyl-phenylamino)-oxazol-5-yl]-benzyl}-2-amino-N-methyl-acetamide;

2-Amino-N-methyl-N-{2-[2-(3-nitro-phenylamino)-oxazol-5-yl]-benzyl}-acetamide;

4-[5-(2-{[(2-Amino-acetyl)-methyl-amino]-methyl}-phenyl)-oxazol-2-ylamino]-benzamide;

2-Amino-N-{2-[2-(4-butyryl-phenylamino)-oxazol-5-yl]-benzyl}-N-methyl-acetamide;

N-{2-[2-(3-Acetylamino-phenylamino)-oxazol-5-yl]-benzyl}-2-amino-N-methyl-acetamide;

3-[5-(2-{[(2-Amino-acetyl)-methyl-amino]-methyl}-phenyl)-oxazol-2-ylamino]-N-methyl-benzamide;

N-{2-[2-(4-Acetylamino-phenylamino)-oxazol-5-yl]-benzyl}-2-amino-N-methyl-acetamide: and 4-[5-(2-{[(2-Amino-acetyl)-methy-amino]-methyl}-phenyl)-oxazol-2-ylamino]-2-methoxy-benzoic acid methyl ester;

or (ii) a pharmaceutically-acceptable salt, hydrate, or prodrug thereof.

12. A pharmaceutical composition comprising an effective amount of at least one compound according to claim 1, or a salt, hydrate or prodrug thereof, and a pharmaceutically acceptable carrier, adjuvant or vehicle.

13. A method for treating an IMPDH-associated disorder, wherein the disorder is selected from arthritis, asthma, inflammation and inhibition of blood coagulation, comprising the step of administering to a subject in need thereof an amount effective therefor of at least one compound of claim 1 or a salt thereof.

* * * * *